(12) United States Patent
Orinski

(10) Patent No.: US 9,079,015 B2
(45) Date of Patent: *Jul. 14, 2015

(54) SYSTEMS AND METHODS FOR MAKING AND USING CONTACT ASSEMBLIES FOR LEADS OF ELECTRICAL STIMULATION SYSTEMS

(71) Applicant: BOSTON SCIENTIFIC NEUROMODULATION CORPORATION, Valencia, CA (US)

(72) Inventor: William George Orinski, Reno, NV (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/532,991

(22) Filed: Nov. 4, 2014

(65) Prior Publication Data

US 2015/0057731 A1    Feb. 26, 2015

Related U.S. Application Data

(63) Continuation of application No. 14/101,861, filed on Dec. 10, 2013, now Pat. No. 8,909,354.

(60) Provisional application No. 61/737,549, filed on Dec. 14, 2012.

(51) Int. Cl.
  *A61N 1/00* (2006.01)
  *A61N 1/05* (2006.01)
  *A61N 1/375* (2006.01)

(52) U.S. Cl.
  CPC ............. *A61N 1/05* (2013.01); *A61N 1/0551* (2013.01); *A61N 1/0553* (2013.01); *A61N 1/3752* (2013.01); *Y10T 29/49117* (2015.01)

(58) Field of Classification Search
  CPC ...... A61N 1/05; A61N 1/0553; A61N 1/3752; A61B 5/0478; A61B 5/0408; A61B 2018/1405
  See application file for complete search history.

(56) References Cited

U.S. PATENT DOCUMENTS 6,181,969 B1  1/2001 Gord
6,516,227 B1  2/2003 Meadows et al.
(Continued)

FOREIGN PATENT DOCUMENTS

WO  2006130202 A2  12/2006
WO  2010144644 A2  12/2010

OTHER PUBLICATIONS

International Search Report and Written Opinion for PCT/US2013/074168 mailed Jun. 3, 2014.
(Continued)

*Primary Examiner* — Robert N Wieland
(74) *Attorney, Agent, or Firm* — Lowe Graham Jones PLLC; Bruce E. Black

(57) ABSTRACT

First contacts are disposed along a distal end portion or a proximal end portion of a lead body of an electrical stimulation lead. A contact assembly is disposed along the other of the distal end portion or the proximal end portion of the lead body. The contact assembly includes a tubular-shaped composite structure formed from multiple layered elements mechanically coupled together and rolled together into a tube. Each of the layered elements includes a first electrically-nonconductive substrate, a second electrically-nonconductive substrate, and micro-circuits laminated therebetween. Second contacts are disposed over the composite structure and electrically coupled to a first end portion of at least one of the micro-circuits. Lead-body conductors electrically couple the first contacts to the second contacts. Each of each of the lead-body conductors is attached to a second end portion of at least one of the micro-circuits.

20 Claims, 17 Drawing Sheets

(56) References Cited

U.S. PATENT DOCUMENTS

| | | |
|---|---|---|
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2007/0150036 A1 | 6/2007 | Anderson |
| 2010/0114276 A1 | 5/2010 | Min et al. |
| 2011/0093052 A1* | 4/2011 | Anderson et al. ............. 607/116 |
| 2013/0123600 A1* | 5/2013 | Tcheng ......................... 600/378 |
| 2014/0130349 A1* | 5/2014 | Swanson et al. ................. 29/885 |

OTHER PUBLICATIONS

Official Communication for U.S. Appl. No. 14/101,861 mailed May 28, 2014.

* cited by examiner

US 9,079,015 B2

SYSTEMS AND METHODS FOR MAKING AND USING CONTACT ASSEMBLIES FOR LEADS OF ELECTRICAL STIMULATION SYSTEMS

CROSS-REFERENCE TO RELATED APPLICATIONS

This application is a continuation of U.S. patent application Ser. No. 14/101,861 filed Dec. 10, 2013, now U.S. Pat. No. 8,909,354, which claims the benefit under 35 U.S.C. §119(e) of U.S. Provisional Patent Application Ser. No. 61/737,549 filed Dec. 14, 2012, both of which are incorporated herein by reference.

FIELD

The present invention is directed to the area of implantable electrical stimulation systems and methods of making and using the systems. The present invention is also directed to implantable electrical stimulation leads having contact assemblies that include micro-circuits formed along layered elements, as well as methods of making and using the leads, micro-circuits, layered elements, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an electrical stimulation lead includes a lead body having a distal end portion and a proximal end portion. A plurality of first contacts is disposed along one of the distal end portion or the proximal end portion of the lead body. A contact assembly is disposed along the other of the distal end portion or the proximal end portion of the lead body. The contact assembly includes a tubular-shaped composite structure that includes a plurality of layered elements mechanically coupled together and rolled into a tube. Each of the plurality of layered elements includes a first electrically-nonconductive substrate, a second electrically-nonconductive substrate, and a plurality of micro-circuits laminated between the first electrically-non-conductive substrate and the second electrically-nonconductive substrate. The micro-circuits each have a first end portion and an opposing second end portion. A plurality of second contacts is disposed over the composite structure. Each of the second contacts is electrically coupled to the first end portion of at least one of the plurality of micro-circuits. A plurality of lead-body conductors electrically couples the plurality of first contacts to the plurality of second contacts. Each of each of the plurality of lead-body conductors is attached to the second end portion of at least one of the plurality of micro-circuits.

In another embodiment, a method of forming an electrical stimulation lead includes extending a plurality of lead-body conductors along a lead body. A plurality of first contacts is electrically coupled to first end portions of the lead-body conductors disposed along a first end portion of the lead body. A plurality of layered elements is formed. Each of the plurality of layered elements includes a plurality of micro-circuits laminated between electrically-nonconductive substrates. Each of the micro-circuits has a first end portion and an opposing second end portion. The plurality of layered elements are coupled together to form a composite structure. Contact interfaces are exposed along the first end portions of each of the plurality of micro-circuits. Conductor interfaces are exposed along the second end portions of each of the plurality of micro-circuits. A second end portion of each of the lead-body conductors is attached to the conductor interface exposed along the second end portion of at least one of the plurality of micro-circuits. A plurality of second contacts is mechanically coupled to the composite structure. Each of the second contacts is electrically coupled to the exposed contact interface of at least one of the plurality of micro-circuits. The composite structure is mechanically coupled to a second end portion of the lead body opposite to the first end portion.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having contact assemblies that include micro-circuits formed along layered elements, as well as methods of making and using the leads, micro-circuits, layered elements, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated herein by reference.

Figure 1:
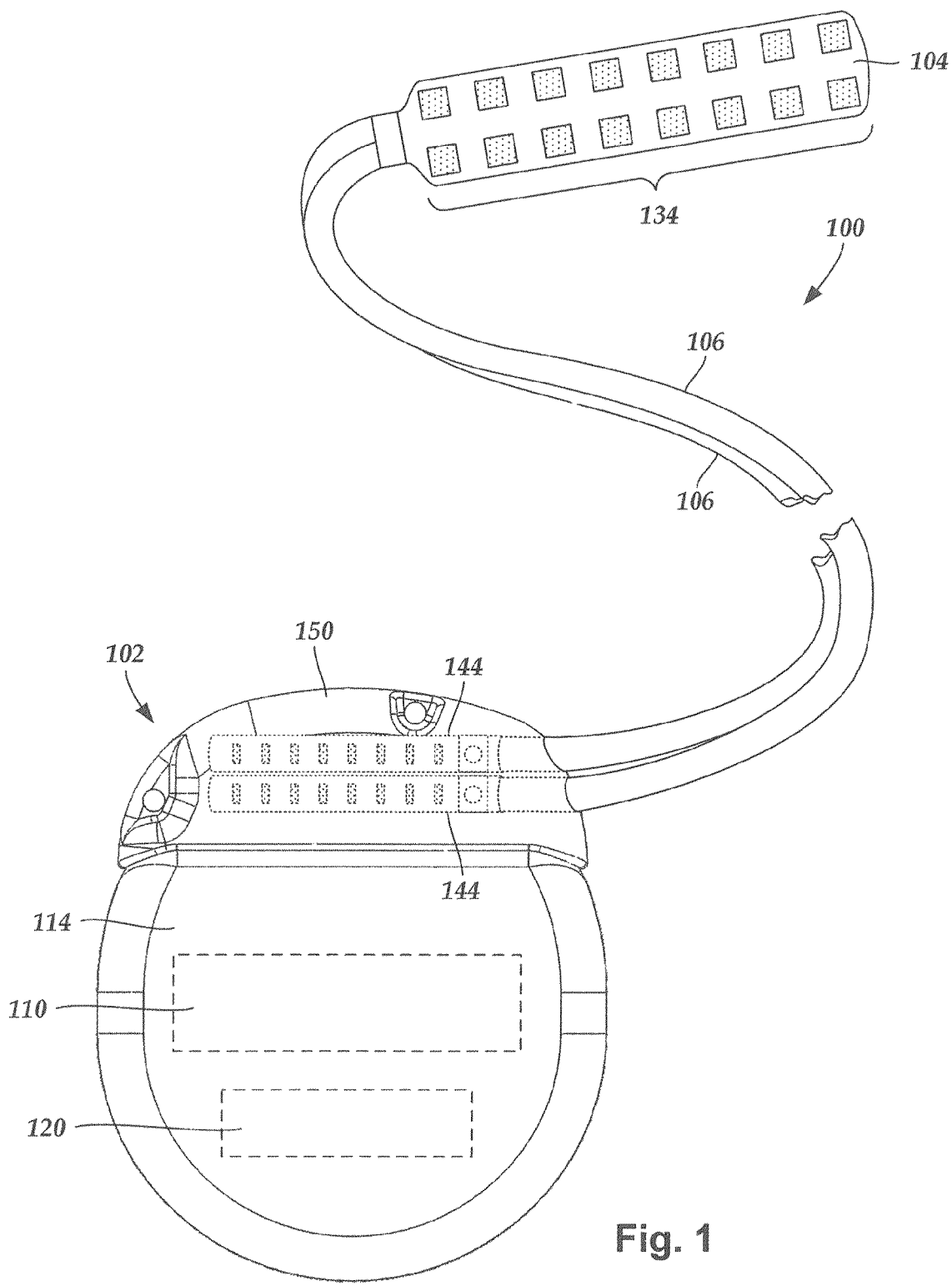
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
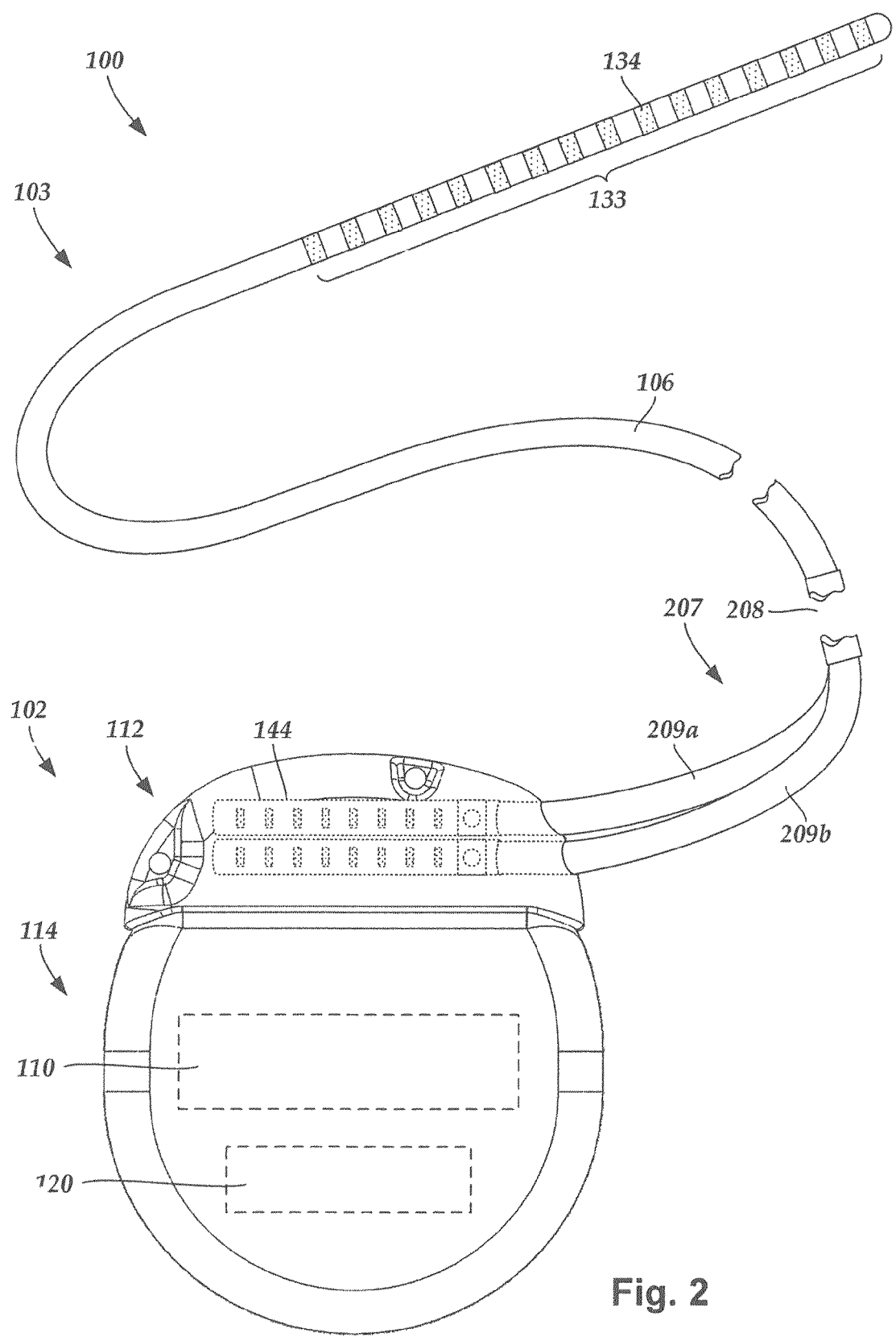
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 and may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
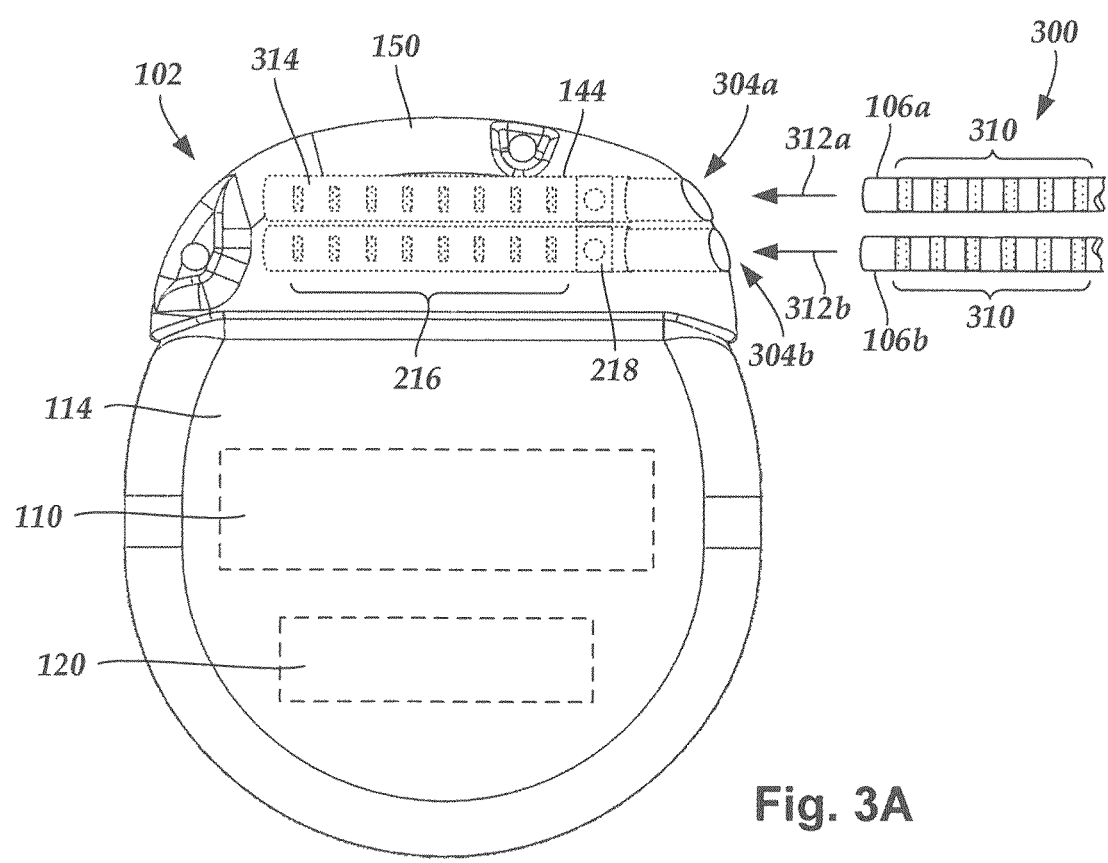
FIG. 3A is a schematic view of one embodiment of the control module of FIG. 1 configured and arranged to electrically couple to an elongated device, according to the invention.
Figure 3B:
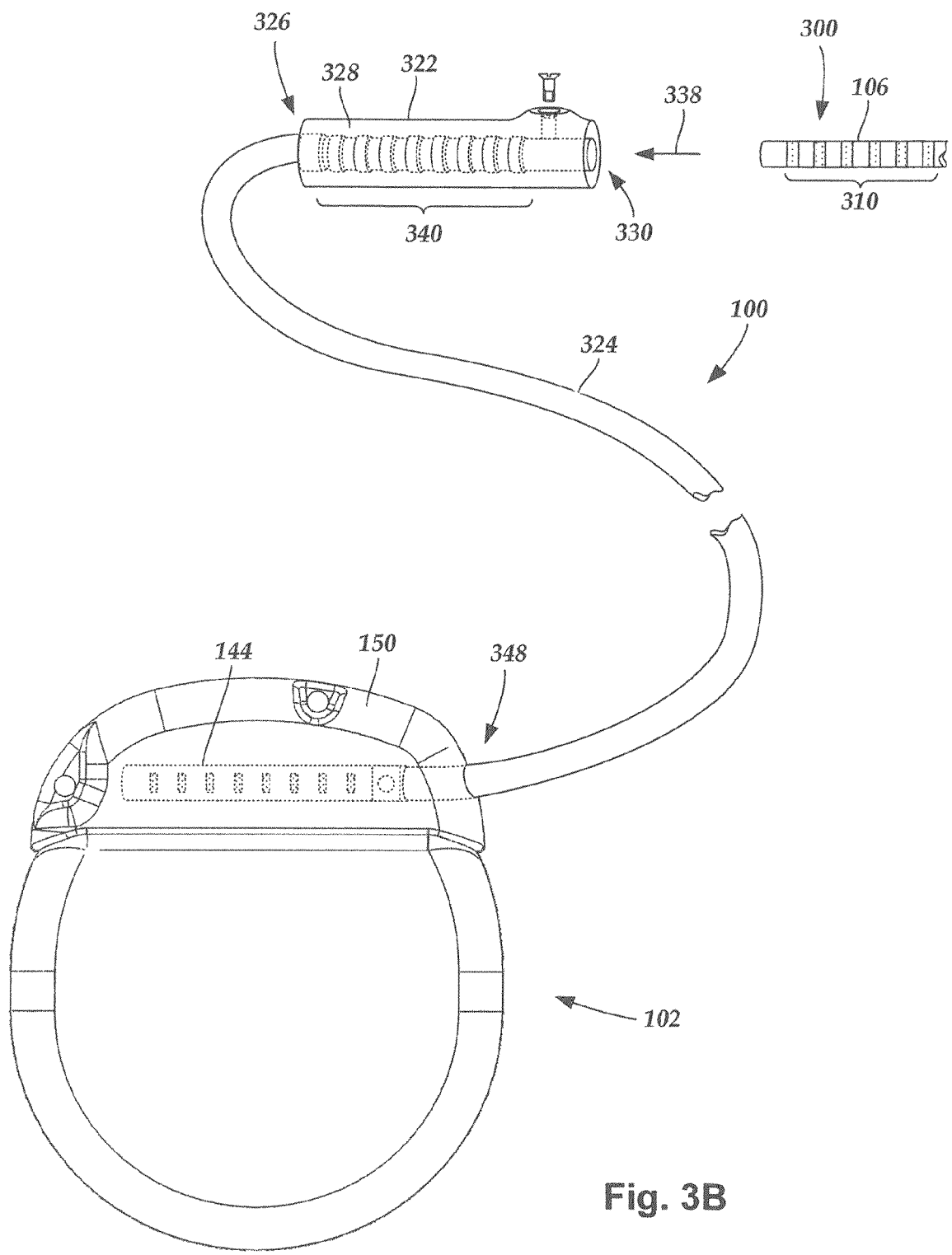
FIG. 3B is a schematic view of one embodiment of a lead extension configured and arranged to electrically couple the elongated device of FIG. 2A to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may also be one or more lumens (not shown) that open at, or near, the distal end of the one or more lead bodies 106, for example, for infusion of drugs or medication into the site of implantation of the one or more lead bodies 106. In at least one embodiment, the one or more lumens may be flushed continually, or on a regular basis, with saline, epidural fluid, or the like. In at least some embodiments, the one or more lumens can be permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 200, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figure 4:
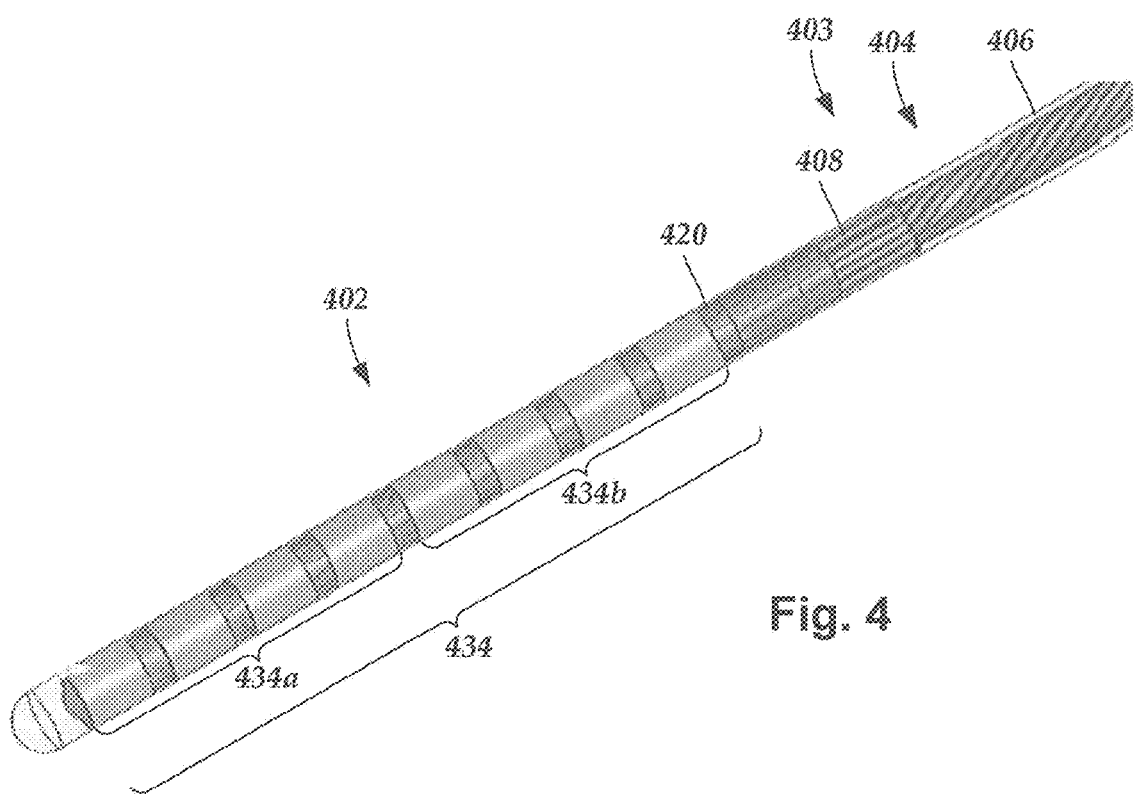
FIG. 4 is a schematic perspective view on one embodiment of an end portion of a lead, the end portion of the lead including a contact assembly and a portion of a lead body, where the contact assembly includes electrodes coupled to micro-circuits of layered elements, and where conductors extending along the lead body are attached to the micro-circuits, according to the invention.

Turning to FIG. 4, contacts (e.g., electrodes and terminals) are typically disposed on end portions of lead bodies. At least some end portions of leads are formed by disposing spacers between adjacent contacts and blind welding lead conductors to the contacts. Such techniques may be expensive and labor intensive. Moreover, such techniques may result in contacts with inconsistent electrical connections between the contacts and the lead conductors.

As herein described, a contact assembly includes contacts disposed along one (or both) of the end portions of the lead body. The contact assemblies also include one or more micro-circuits (e.g., conductive traces, or the like) that electrically couple the contacts to conductors extending along the lead body. Providing micro-circuits may enable a simpler, more reliable and consistent electrical connection to be made between the contacts and the lead conductors. Additionally, micro-circuits may simplify the manufacturing process and reduce costs associated therewith.

The micro-circuits of the enhanced contact assemblies may be disposed on layered elements (e.g., conductive traces laminated between electrically-non-conductive substrates). In at least some embodiments, the layered elements are formed from micro-circuit frames that include multiple electrically-isolated micro-circuits arranged into particular configurations.

FIG. 4 provides one embodiment of a contact assembly 402. The contact assembly 402 illustrated in FIG. 4 is formed along a distal end portion of a percutaneous lead. It will be understood, however, that the contact assembly disclosed herein can be formed, for example, along either (or both) a distal end portion or a proximal end portion of a percutaneous lead. Additionally, the contact assembly may be disposed, for example, along a proximal end portion of a paddle lead.

FIG. 4 is a schematic perspective view of one embodiment of the contact assembly 402 coupled to a distal end portion 404 of a lead 403. The lead 403 includes a lead body 406 and multiple lead-body conductors 408 extending along the lead body 406. The contact assembly 402 includes a body 420 and electrodes 434 disposed along the body 420. In FIG. 4, the electrodes 434 are shown divided into two groupings: distal electrodes, such as distal electrode 434a; and proximal electrodes, such as proximal electrode 434b.

As will be discussed in more detail below, the body 420 is formed from one or more layered elements, such as first layered element (see e.g., 652 of FIG. 6B) and second layered element (see e.g., 952 of FIG. 9) coupled together to form a composite structure (see e.g., 1002 of FIG. 10). Additionally, in at least some embodiments the distal electrodes 434a are coupled to the first layered element, and the proximal electrodes 434b are coupled to the second layered element. When the electrodes 434 are divided into multiple groupings, such as the distal electrodes 434a and the proximal electrodes 434b, the number of electrodes within each grouping can be equal to one another, or can be unequal to one another. In FIG. 4, and in other figures, the number of distal electrodes 434a is equal to the number of proximal electrodes 434b.

FIGS. 5A-16 disclose one embodiment of forming the contact assembly 402 using layered elements. In the embodiment shown in FIGS. 5A-16, the contact assembly is formed using two layered elements, where micro-circuits of one of the layered elements are electrically coupled to the distal electrodes 434a, and micro-circuits of the other of the layered elements are electrically coupled to proximal electrodes 434b. The embodiment described in FIGS. 5A-16 additionally includes: mechanically coupling the layered elements to one another to form a composite structure; electrically coupling the micro-circuits to the lead-body conductors; mechanically coupling the electrodes to the composite structure; and mechanically coupling the composite structure to the lead body.

Figure 5A:
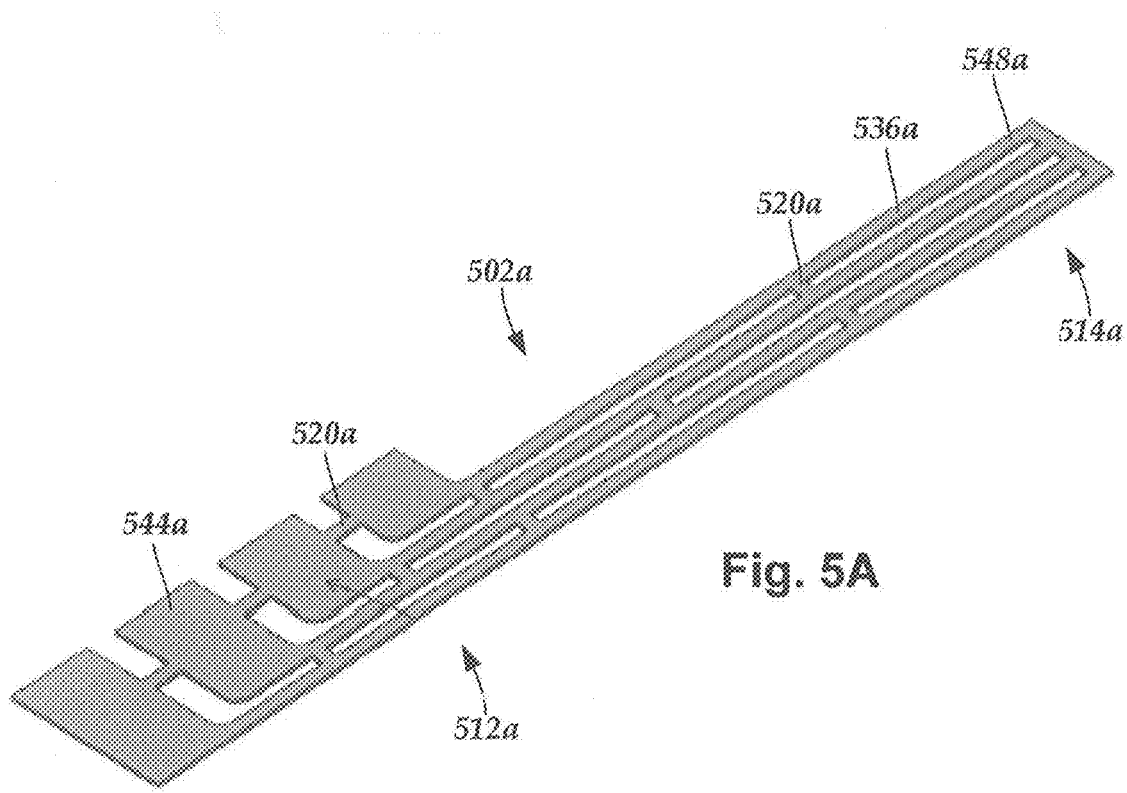
FIG. 5A is a schematic perspective view of one embodiment of a first micro-circuit frame that includes at least some of the micro-circuits of the contact assembly of FIG. 4, according to the invention.
Figure 5B:
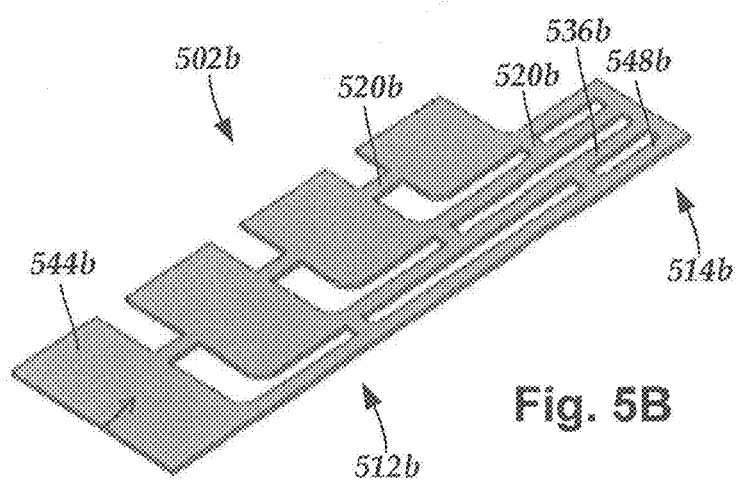
FIG. 5B is a schematic perspective view of one embodiment of a second micro-circuit frame that includes at least some of the micro-circuits of the contact assembly of FIG. 4, according to the invention.

FIG. 5A is a schematic perspective view of one embodiment of a first micro-circuit frame 502a suitable for use in the contact assembly 402. FIG. 5B is a schematic perspective view of one embodiment of a second micro-circuit frame 502b suitable for use, along with the first micro-circuit frame 502a, in the contact assembly 402.

The first micro-circuit frame 502a includes one or more micro-circuits, such as the micro-circuit 536a; and the second micro-circuit frame 502b includes one or more micro-circuits, such as the micro-circuits 536b. In at least some embodiments, the micro-circuits 536a are formed as a plurality of individual conductive traces that extend generally parallel to one another along the first micro-circuit frame 502a. Similarly, in at least some embodiments the micro-circuits 536b are formed as a plurality of individual conductive traces that extend generally parallel to one another along the second micro-circuit frame 502b.

The micro-circuits 536a and 536b are configured and arranged to electrically couple contacts, such as the electrodes 434, to lead-body conductors 408. In at least some embodiments, each contact is coupled to a different micro-circuit. In at least some other embodiments, at least one of the micro-circuits is coupled to at least two different contacts. In at least some embodiments, at least one contact is coupled to at least two micro-circuits.

The micro-circuits 536a and 536b can be formed from any electrically-conductive material suitable for implantation including, for example, metals, alloys, conductive polymers, conductive carbon, or the like. In at least some embodiments, the micro-circuits 536a and 536b are formed from MP35N.

The micro-circuits 536a may, optionally, be coupled to one another by tie bars 520a. Similarly, in at least some embodiments the micro-circuits 536b may, optionally, be coupled to one another by tie bars 520b. In which case, the tie bars 520a and 520b are preferably rigid to maintain a constant spacing between adjacent micro-circuits 536a and 536b.

It may be advantageous for the micro-circuits 536a and 536b to be coupled to one another by one or more tie bars 520a and 520b, respectively, to maintain a constant spacing between adjacent micro-circuits. It may further be advantageous to use tie bars 520a and 520b to facilitate manufacture of the first and second micro-circuit frames 502a and 502b, respectively. For example, in at least some embodiments the micro-circuit frames 502a and 502b are stamped. In at least some embodiments, the micro-circuit frames 502a and 502b are chem-etched.

The micro-circuits 536a each have a first end portion 512a and an opposing second end portion 514a. The first end portions 512a are configured and arranged to couple to contacts, such as the electrodes 434a. The second end portions 514a are configured and arranged to attach to lead-body conductors, such as the lead-body conductors 408.

In at least some embodiments, contact interfaces, such as first contact interface 544a, are disposed along the first end portions 512a of the micro-circuits 536a of the first micro-circuit frame 502a. In at least some embodiments individual first contact interfaces 544a are spaced apart from one another with a pitch (i.e., the distances between centers of adjacent first contact interfaces 544a) that corresponds with the pitch of the electrodes 434a of the contact assembly 402. In at least some embodiments, a different first contact interface 544a is disposed along the first end portion 512a of each micro-circuit 536a of the first micro-circuit frame 502a. In at least some embodiments, adjacent first contact interfaces 544a are coupled to one another via at least one of the tie bars 520a.

Similarly, the micro-circuits 536b each have a first end portion 512b and an opposing second end portion 514b. The first end portions 512b are configured and arranged to couple to contacts, such as the electrodes 434b. The second end portions 514b are configured and arranged to attach to lead-body conductors, such as the lead-body conductors 408.

In at least some embodiments, second contact interfaces, such as second contact interface 544b, are disposed along the first end portions 512b of the micro-circuits 536b of the second micro-circuit frame 502b. In at least some embodiments the individual second contact interfaces 544b are spaced apart from one another with a pitch (i.e., the distances between centers of adjacent second contact interfaces 544b) that corresponds with the pitch of the electrodes 434b of the contact assembly 402. In at least some embodiments, a different second contact interface 544b is disposed along the first end portion 512b of each micro-circuit 536b of the second micro-circuit frame 502b. In at least some embodiments, adjacent second contact interfaces 544b are coupled to one another via at least one tie bar 520b.

In at least some embodiments, first conductor interfaces, such as first conductor interface 548a, are disposed along the second end portions 514a of the micro-circuits 536a of the first micro-circuit frame 502a. Similarly, in at least some embodiments second conductor interfaces, such as second conductor interface 548b, are disposed along the second end portions 514b of the micro-circuits 536b of the first micro-circuit frame 502b.

Turning to FIGS. 6A-8B, in at least some embodiments the micro-circuit frames 502a and 502b are laminated between sheets of electrically-insulative material; the individual micro-circuits of the micro-circuit frames 502a and 502b are electrically isolated from one another; and portions of the electrically-insulative material are removed at the first and second ends of the micro-circuits to facilitate coupling of the micro-circuit frames 502a and 502b to the electrodes 434 and to the lead-body conductors 408. In FIGS. 6A-8B, these steps are discussed solely with regards to the micro-circuit frame 502a. It will be understood that, in at least some embodiments, the same steps occur with regards to the micro-circuit frame 502b.

Figure 6A:
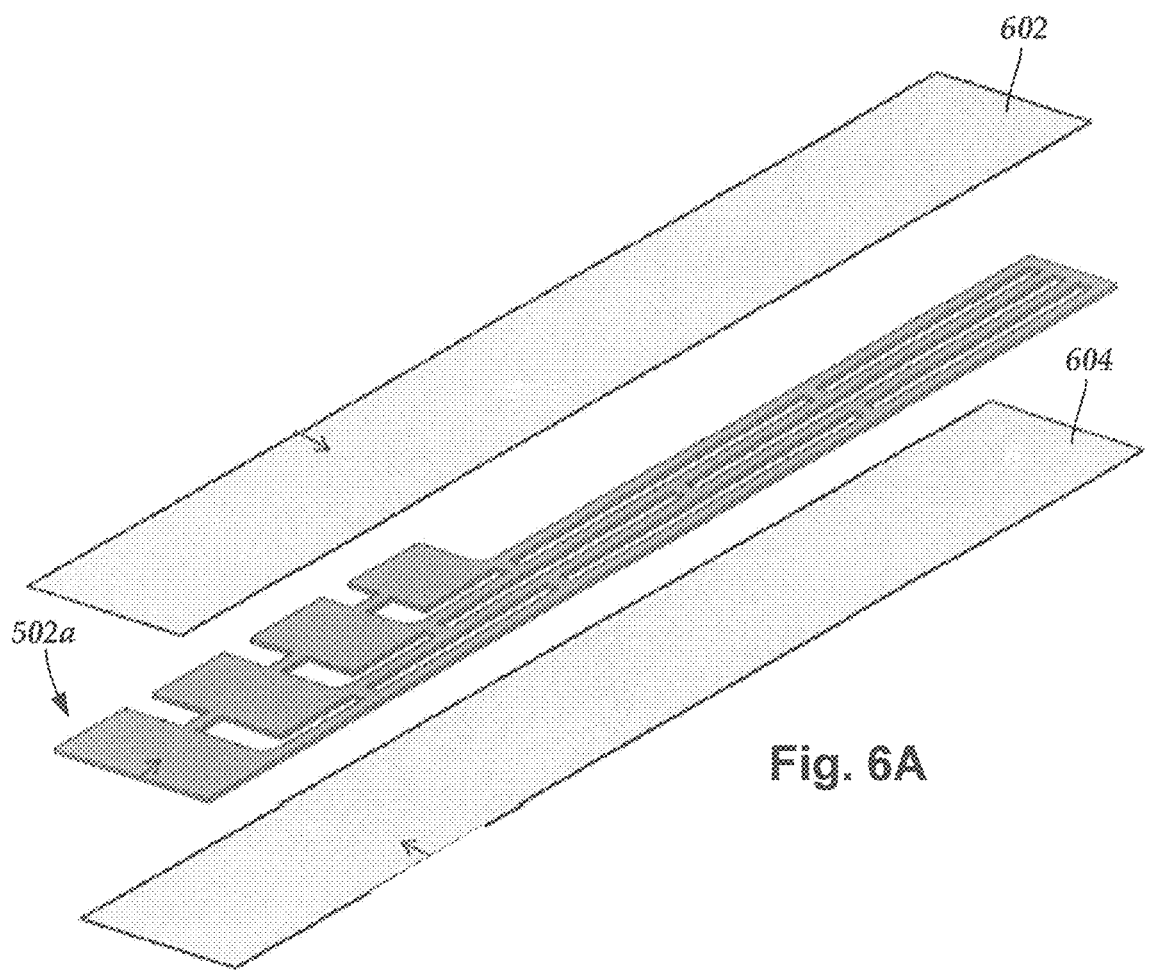
FIG. 6A is a schematic perspective view of one embodiment of the first micro-circuit frame of FIG. 5A and first and second insulative substrates configured and arranged for disposing over opposing major surfaces of the first micro-circuit frame, according to the invention.

FIG. 6A is a schematic perspective view of one embodiment of the first micro-circuit frame 402a, a first electrically-insulative substrate 602, and a second electrically-insulative substrate 604. The first and second electrically-insulative substrates 602 and 604 are configured and arranged for disposing over opposing major surfaces of the first micro-circuit frame 402a.

The electrically-insulative substrates 602 and 604 may be formed from any electrically-insulative materials suitable for implantation. In at least some embodiments, one or more of the electrically-insulative substrates 602 and 604 is formed from a film. It may be advantageous to use a film to facilitate removal of air pockets between the electrically-insulative substrates 602 and 604. Films may also provide flexibility that facilitates the manufacturing process.

In at least some embodiments, one or more of the electrically-insulative substrates 602 and 604 is formed from a material suitable for re-flowing including, for example, one or more thermoplastics (e.g., Pellethane®, or the like). As will be discussed in more detail below, the micro-circuit frames and electrically-insulative substrates are formed into layered elements that are coupled to one another. Although the layered elements may be coupled together using any suitable techniques (e.g., applying adhesives, or the like), it may be advantageous to re-flow the material of the electrically-insulative substrates to enable the multiple layered elements to form a more uniform, cohesive structure.

Figure 6B:
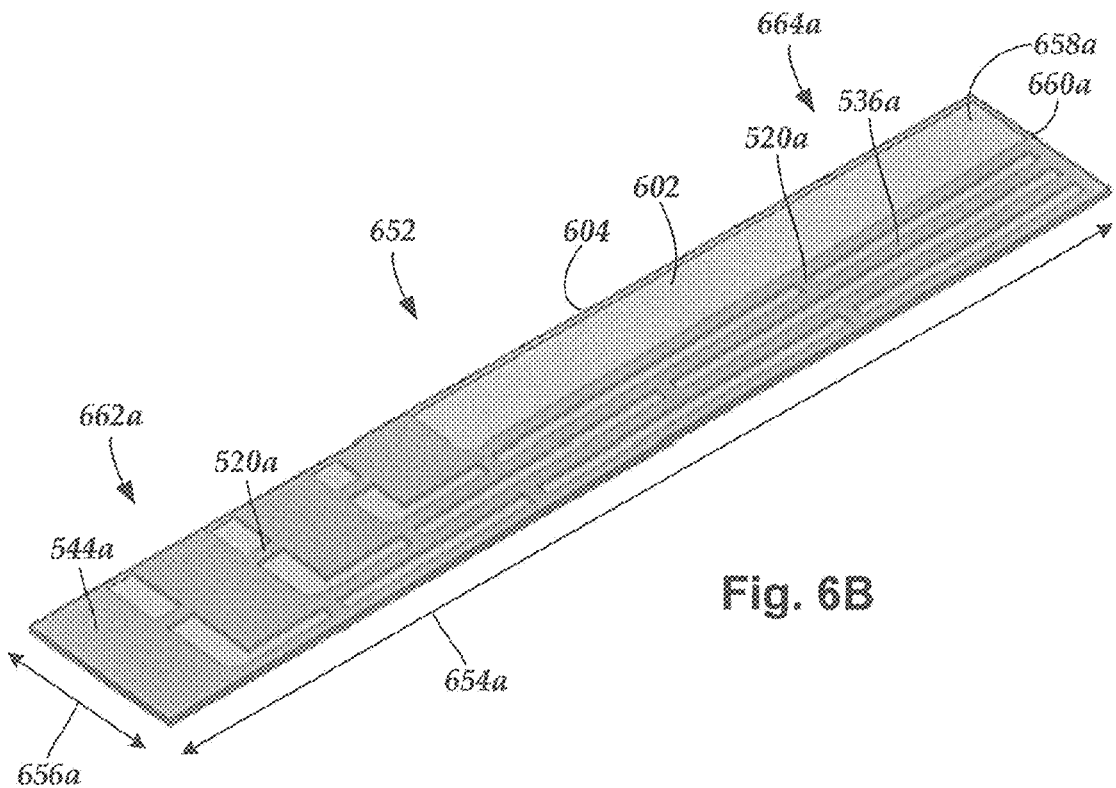
FIG. 6B is a schematic perspective view of one embodiment of a first layered element formed by laminating the first and second insulative substrates of FIG. 6A over the first micro-circuit frame of FIG. 5A, according to the invention.

FIG. 6B is a schematic perspective view of one embodiment of a first layered element 652 formed by laminating the first micro-circuit frame 502a between the first electrically-insulative substrate 602 and the second electrically-insulative substrate 604. As shown in FIG. 6B, the first layered element 652 has a length 654a, a width 656a, a first major surface 658a, an opposing second major surface 660a, a first end portion 662a, and a second end portion 664a. In at least some embodiments, at least one of the electrically-insulative substrates 602 and 604 is formed from a material that is transparent or translucent enough so that the contact interfaces 544a are visible through at least one of the electrically-insulative substrate 602 or 604.

Figure 7:
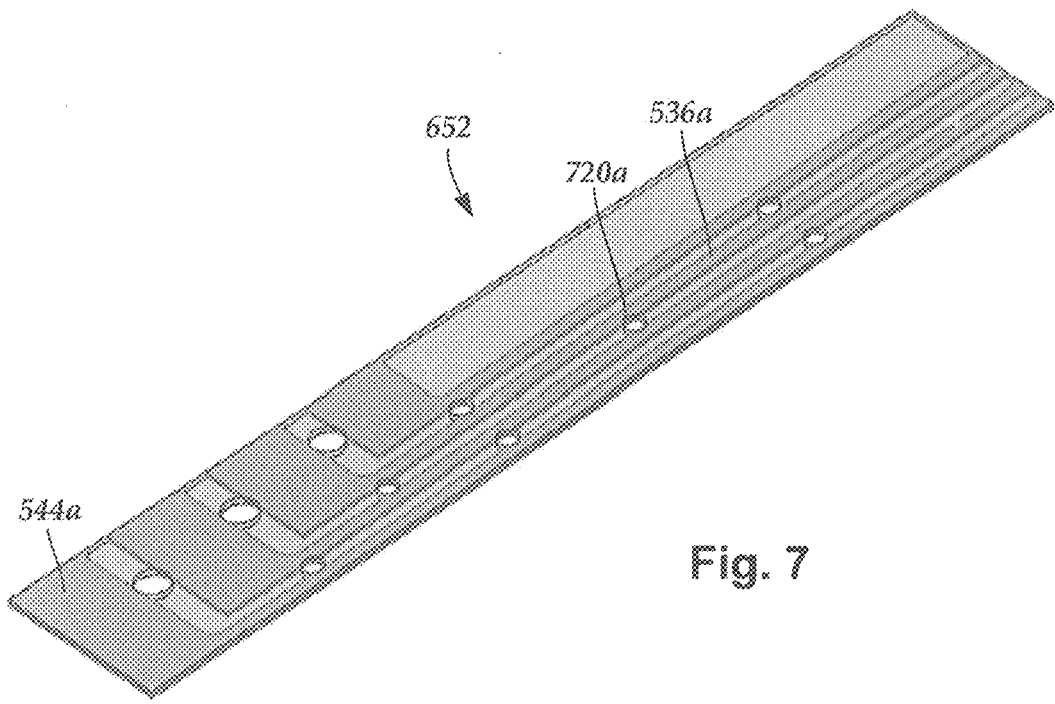
FIG. 7 is a schematic perspective view of one embodiment of the first layered element of FIG. 6B, where tie bars formerly coupling together adjacent micro-circuits of the first layered element have been removed to electrically isolate adjacent micro-circuits from one another, according to the invention.

Turning to FIG. 7, in at least some embodiments once the micro-circuits are laminated, the tie bars 520a coupling together adjacent micro-circuits are severed. FIG. 7 is a schematic perspective view of one embodiment of the first layered element 652. In at least some embodiments, the tie bars 520a (see e.g., FIG. 6B) are severed, thereby electrically-isolating each of the micro-circuits 536a from one another. The tie bars 520a can be severed using any suitable technique including, for example, punching, laser cutting, drilling, or the like. In FIG. 7 (and in other figures) severed tie bars 520a are shown as circles. In at least some embodiments, when the tie bars 520a are severed, one or more severed ends 720a of the tie bars 520a remain attached to at least some of the individual micro-circuits.

Figure 8A:
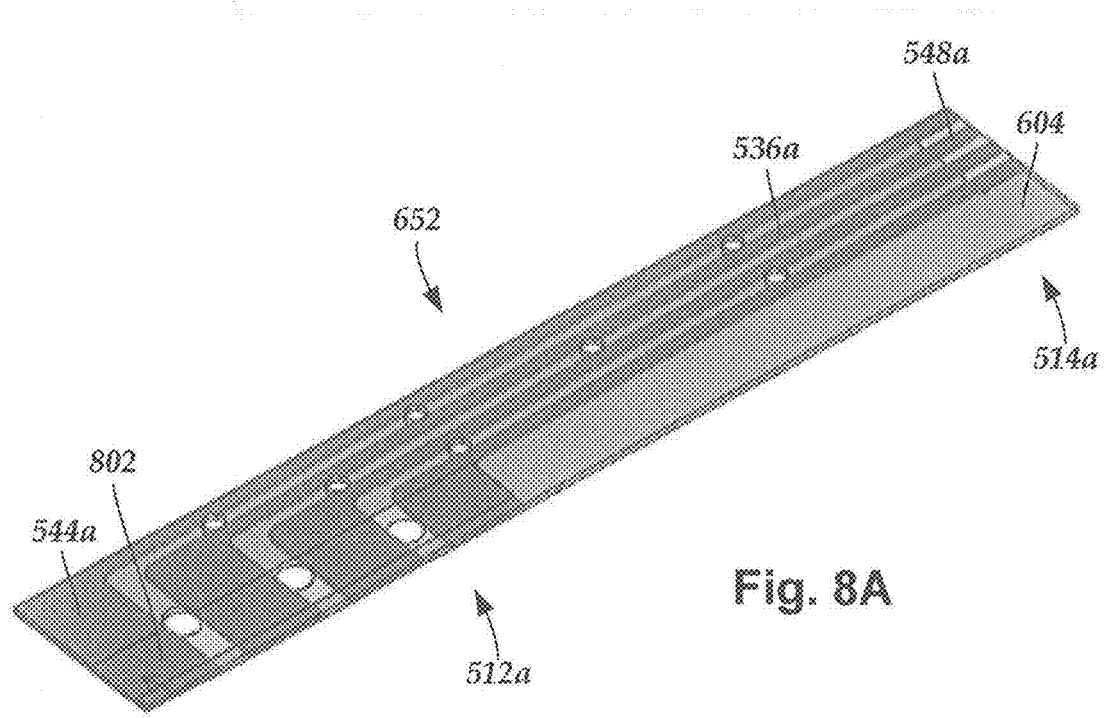
FIG. 8A is a schematic perspective view of one embodiment of the first layered element of FIG. 7, where portions of at least one of the insulative substrates of FIG. 6A are removed to expose contact interfaces along first ends of micro-circuits of the first layered element, according to the invention.
Figure 8B:
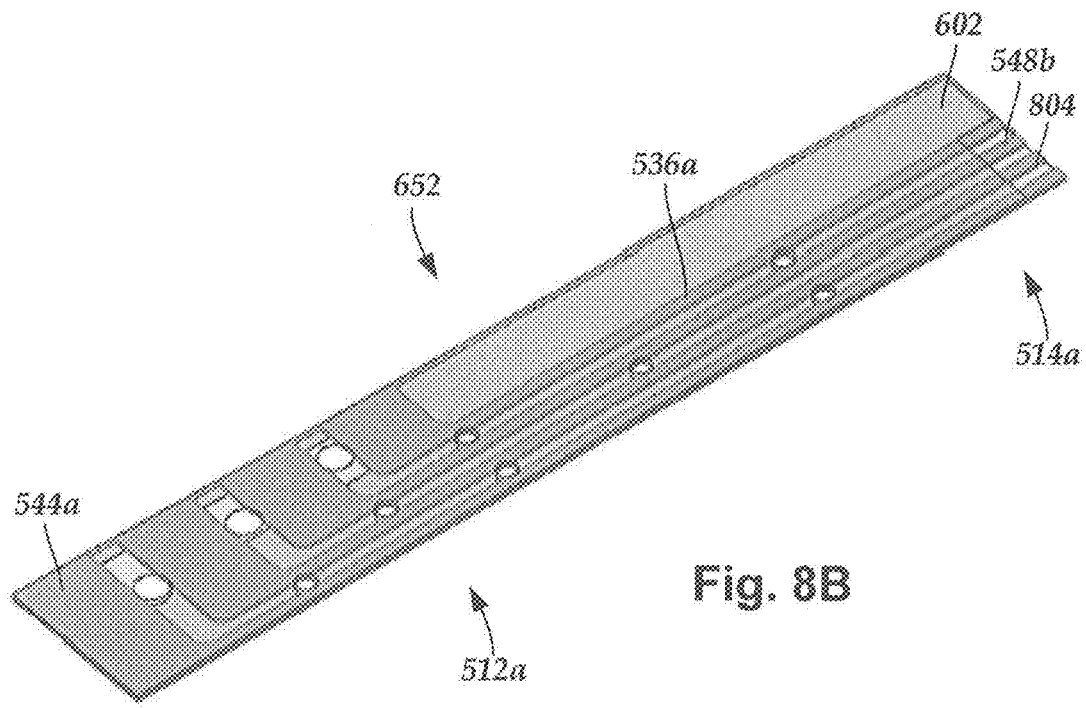
FIG. 8B is a schematic perspective view of one embodiment of the first layered element of FIG. 7, where portions of at least one of the insulative substrates of FIG. 6A are removed to expose conductor interfaces along second ends of micro-circuits of the first layered element, according to the invention.

Turning to FIGS. 8A-8B, portions of the electrically-insulative substrates 602 and 604 disposed over the first and second portions 512a and 514a of the micro-circuits 536a can be removed to expose surfaces of the micro-circuits for coupling to the electrodes and to the lead-body conductors. FIGS. 8A and 8B are schematic perspective views of one embodiment of the first layered element 652. As shown in FIG. 8A, at least one portion of the second electrically-insulative substrate 604 is removed along the first end portion 512a of the first layered element 652 to expose portions 802 of each of the micro-circuits 536a at their respective first contact interfaces 544a. As mentioned above, the exposed portions of the first contact interfaces 544a provide surfaces for coupling to contacts, such as the electrodes 434a.

As shown in FIG. 8B, at least one portion of the first electrically-insulative substrate 602 is removed along the second end portion 514a of the first layered element 652 to expose portions 804 of each of the micro-circuits 536a at their respective conductor interfaces 548a. As mentioned above, the exposed portions of the conductor interfaces 548a provide surfaces for attaching to conductors, such as the lead-body conductors 408.

It will be understood that either (or both) of the electrically-insulative substrates 602 and 604 may be removed at either (or both) of the interfaces 544a and 548a. It will also be understood that the electrically-insulative substrates 602 and 604 can be removed to expose the micro-circuits 536a at the interfaces 544a and 548a in any suitable manner including, for example, laser ablation.

Figure 9:
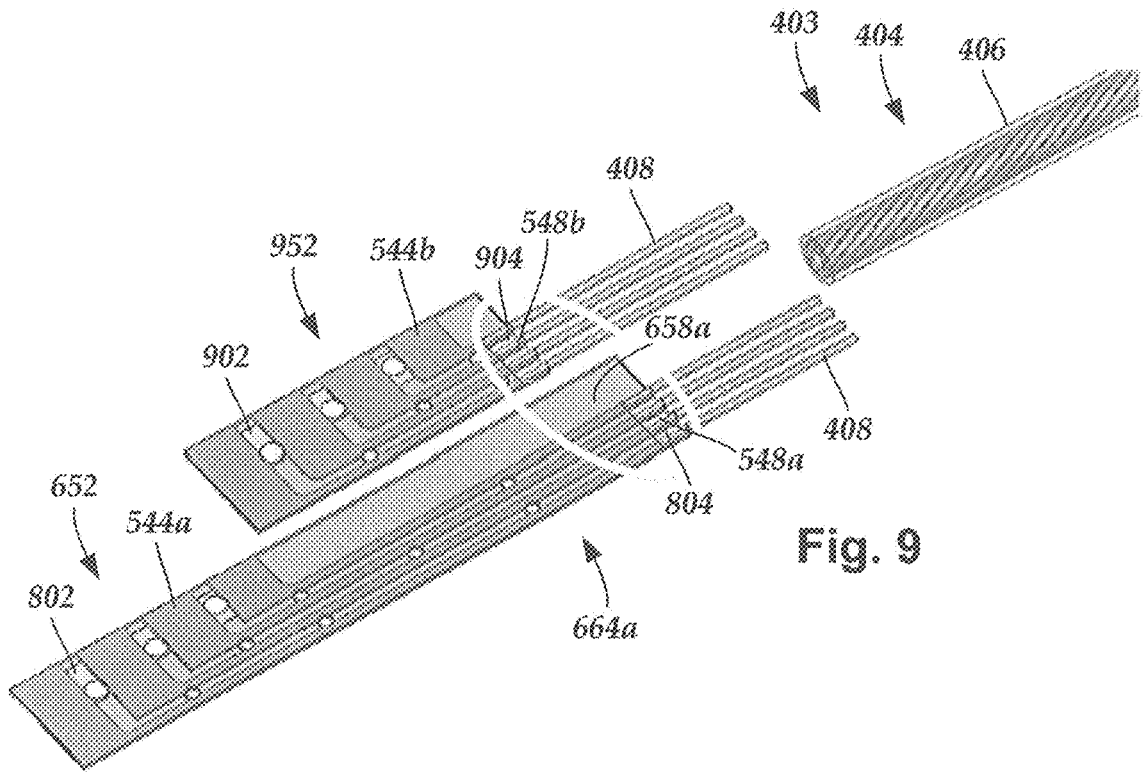
FIG. 9 is a schematic perspective view of one embodiment of an end portion of the lead body of FIG. 4, the first layered element of FIG. 8B, and a second layered element formed using the second micro-circuit frame of FIG. 5B, where lead-body conductors are attached to micro-circuits of the first and second layered elements along conductor interfaces and are configured for insertion into the lead body, according to the invention.

Turning to FIG. 9, once the micro-circuits are exposed at their respective conductor interfaces, the micro-circuits can be attached to the lead-body conductors. FIG. 9 is a schematic perspective view of one embodiment of an end portion of the lead body 406, the first layered element 652, and a second layered element 952 formed using the second micro-circuit frame 502b.

The second layered element 952 can be formed by performing similar steps to the second micro-circuit frame 502b as described in relation to the first micro-circuit frame 502a in FIGS. 6A-8B. For example, as shown in FIG. 9 the second micro-circuit frame 502a is laminated between electrically-insulative substrates; the tie bars 520b of the second micro-circuit frame 502a are severed; and portions of the electrically-insulative substrates disposed over the first and second portions 512b and 514b, respectively, of the micro-circuits 536b are removed to expose portions 902 and 904 of the micro-circuits 536b for coupling to the electrodes and to the lead-body conductors 408, respectively. In at least some embodiments, as with the first micro-circuit frame 520a, when the tie bars 520b of the second micro-circuit frame 502b are severed, one or more severed ends of the tie bars 520b remain attached to at least some of the individual micro-circuits.

In FIG. 9, some of the lead-body conductors 408 are shown attached to the exposed portions 804 of the first layered element 652 at the conductor interfaces 548a, and some of the lead-body conductors 408 are shown attached to the exposed portions 904 of the second layered element 952 at the conductor interfaces 548b. In FIG. 9 (and in other figures), an equal number of lead-body conductors 408 are coupled to each of the layered elements 652 and 952. In other embodiments, a different number of lead-body conductors 408 are coupled to each of the layered elements 652 and 952.

The lead-body conductors 408 can be attached to the exposed portions 804 and 904 of the first and second layered elements 652 and 952, respectively, in any suitable manner including, for example, laser welding, crimping, resistance welding, or the like or combinations thereof. In at least some embodiments, the layered elements 652 and 952 include one or more cable crimp lugs for facilitating attachment of the lead-body conductors 408 to the exposed portions 804 and 904 of the first and second layered elements 652 and 952, respectively.

In FIG. 9 (and in other figures), the lead-body conductors 408 are shown attached to the layered elements 652 and 952 prior to being extended along the lead body 406. It will be understood that the lead-body conductors 408 can be attached to the layered elements 652 and 952 either before or after the lead-body conductors 408 are extended along the lead body 406.

Figure 10:
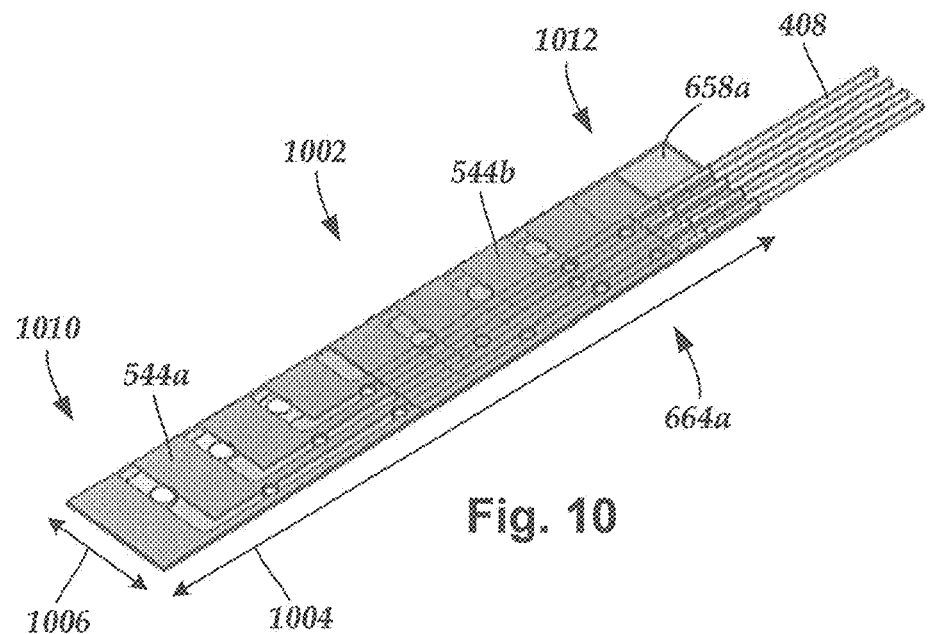
FIG. 10 is a schematic perspective view of one embodiment of the first layered element of FIG. 9, the second layered element of FIG. 9, and the lead-body conductors of FIG. 9 coupled to micro-circuits of the first and second layered elements, where the second layered element is stacked onto, and coupled to, the first layered element to form a composite structure, according to the invention.

Turning to FIG. 10, in at least some embodiments the layered elements are mechanically coupled to one another to form a composite structure. FIG. 10 is a schematic perspective view of one embodiment of a composite structure 1002 having a length 1004, a width 1006, a first end portion 1010, and a second end portion 1012. The composite structure 1002 is formed by coupling together the first layered element 652 and the second layered element 952.

In at least some embodiments, the first layered element 652 and the second layered element 952 are coupled together into an arrangement where the second layered element 952 is stacked on top of the second end portion 664a of the first major surface 658a of the first layered element 652. In which case, in at least some embodiments the lead-body conductors 408 attached to the layered elements 652 and 952 are also stacked into at least two layers. In at least some embodiments, the second layered element 952 is stacked onto the first layered element 652 such that the contact interfaces 544a and 544b are equally spaced-apart from one another along the length 1004 of the composite structure 1002. As shown in FIGS. 9 and 10, in at least some embodiments the first layered element 652 and the second layered element 952 have different lengths.

The first layered element 652 and the second layered element 952 can be coupled together in any suitable manner including, for example, one or more adhesives, re-flowing, or the like. It may be advantageous to couple the first layered element 652 and the second layered element 952 together by re-flowing the material of the electrically-insulative substrates to enable the composite structure 1002 to form a more uniform, cohesive structure.

Figure 11:
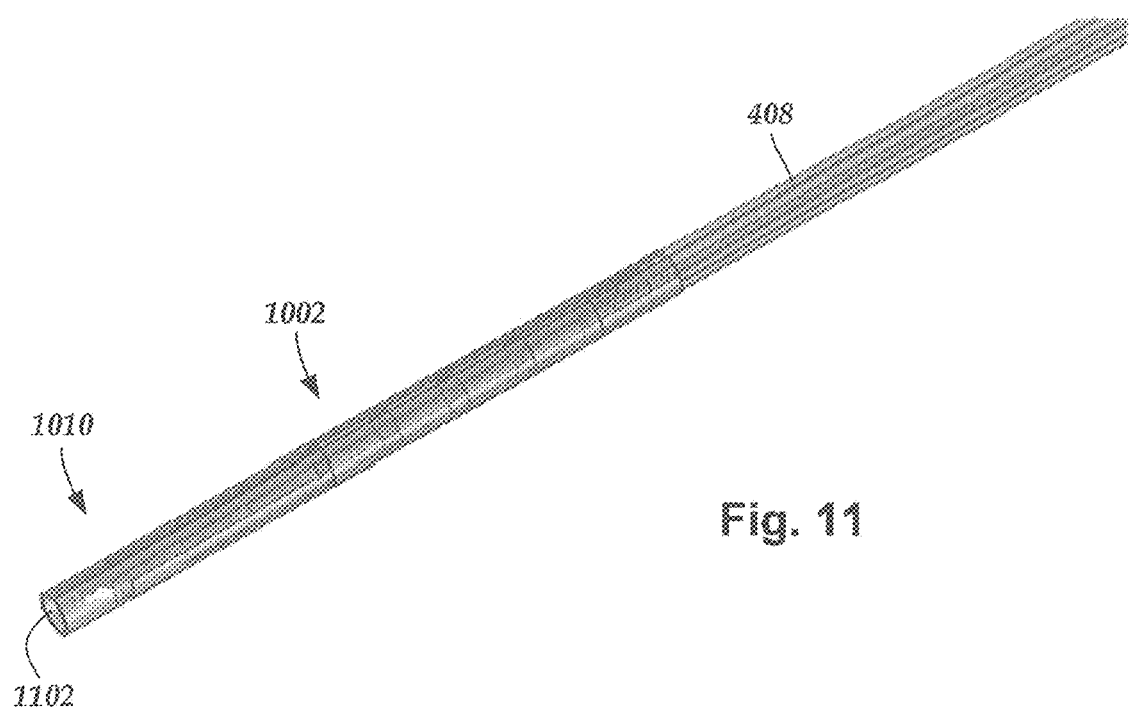
FIG. 11 is a schematic perspective view of one embodiment of the lead-body conductors of FIG. 10 attached to the composite structure of FIG. 10, where the lead-body conductors are attached to micro-circuits of the composite structure, and where the composite structure is rolled into a tube, according to the invention.

Turning to FIG. 11, the composite structure 1002 may be formed into a shape that facilitates electrically coupling of contacts, such as the electrodes 434, to the composite structure. FIG. 11 is a schematic perspective view of one embodiment of the composite structure 1002. The lead-body conductors 408 are attached to the micro-circuits 536a and 536b of the composite structure 1002. In FIG. 11, the composite structure is shown rolled into a tube. In FIG. 11, the composite structure 1002 is rolled about the length 1004 of the composite structure 1002 such that the width 1006 of the composite structure 1002 forms a circumference of the tube-shaped composite structure 1002. The rolled-up composite structure 1002 forms a bore 1102 extending along the composite structure 1002. In at least some embodiments, at least a portion of the bore 1102 forms an end portion of a stylet lumen that extends along the lead body 406.

In alternate embodiments, the stacked composite structure 1002 is formed into other shapes configured and arranged for facilitating electrically coupling of contacts, such as the electrodes 434, to the composite structure. For example, in at least some embodiments the composite structure 1002 is folded into pleats, thereby forming an accordion-like structure.

Figure 12A:
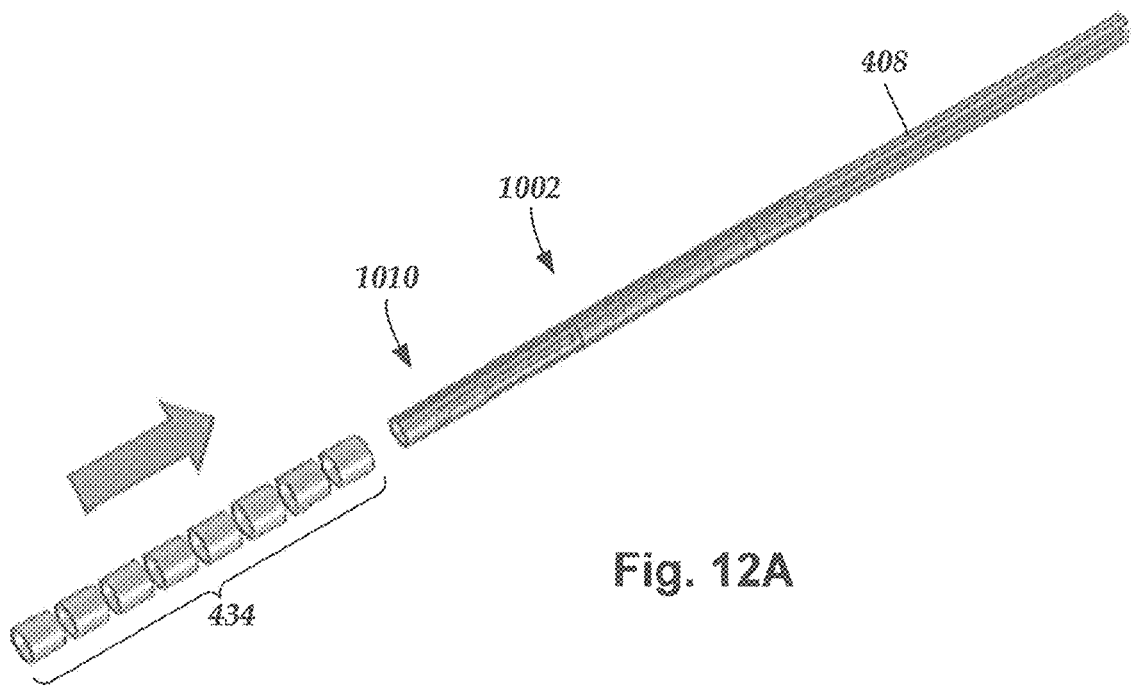
FIG. 12A is a schematic perspective view of one embodiment of ring-shaped electrodes and the lead-body conductors of FIG. 11 attached to the composite structure of FIG. 11, where the electrodes are configured and arranged for disposing over the composite structure, according to the invention.
Figure 12B:
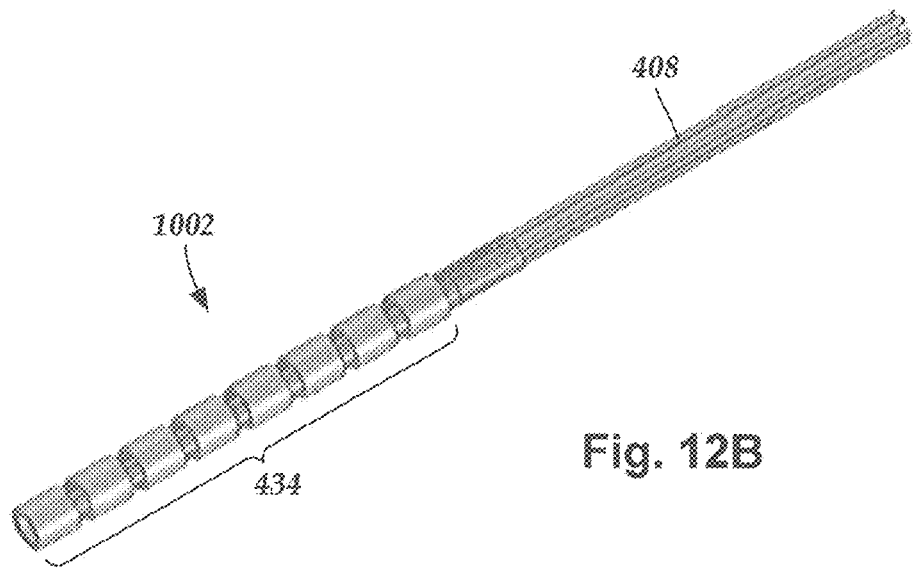
FIG. 12B is a schematic perspective view of one embodiment of the lead-body conductors of FIG. 12A attached to the composite structure of FIG. 12A, where the electrodes of FIG. 12A are disposed over portions of the composite structure, according to the invention.

Turning to FIGS. 12A-12B, contacts, such as the electrodes 434, can be electrically coupled to the micro-circuits of the composite structure 1002. FIG. 12A is a schematic perspective view of one embodiment of the composite structure 1002 and the electrodes 434. In FIG. 12A, the lead-body conductors 408 are shown attached to the micro-circuits (536a and 536b in FIGS. 5A-5B) of the composite structure 1002.

The electrodes 434 are configured and arranged for electrically coupling to the micro-circuits (536a and 536b in FIGS. 5A-5B) of the composite structure 1002. In FIG. 12A, the electrodes 434 are shown as being ring-shaped. It will be understood that the electrodes 434 can be any suitable shape including, for example, C-shaped, segmented, or the like. In FIG. 12A, the composite structure 1002 is shown rolled into a tube-shaped structure configured and arranged for passing through the bore of ring-shaped electrodes 434.

FIG. 12B is a schematic perspective view of one embodiment of the composite structure 1002 and the electrodes 434. In FIG. 12A, the lead-body conductors 408 are shown attached to the micro-circuits (536a and 536b in FIGS. 5A-5B) of the composite structure 1002. The electrodes 434 are disposed over portions of the composite structure 1002. In at least some embodiments, such as when the electrodes 434 are ring-shaped, the electrodes 434 are slid over the first end portion 1010 of the composite structure 1002. As shown in FIG. 12B, in at least some embodiments the electrodes 434 are disposed over the composite structure 1002 such that the electrodes 434 are spaced apart from one another and aligned with the contact interfaces 544a and 544b of the composite structure 1002.

In at least some embodiments, the electrodes 434 are visually aligned with the contact interfaces 544a and 544b of the composite structure 1002. As mentioned above, in at least some embodiments at least one of the electrically-insulative substrates 602 and 604 is formed from a material that is transparent or translucent enough so that the contact interfaces 544a and 544b are visible through at least one of the electrically-insulative substrate 602 or 604.

Figure 13A:
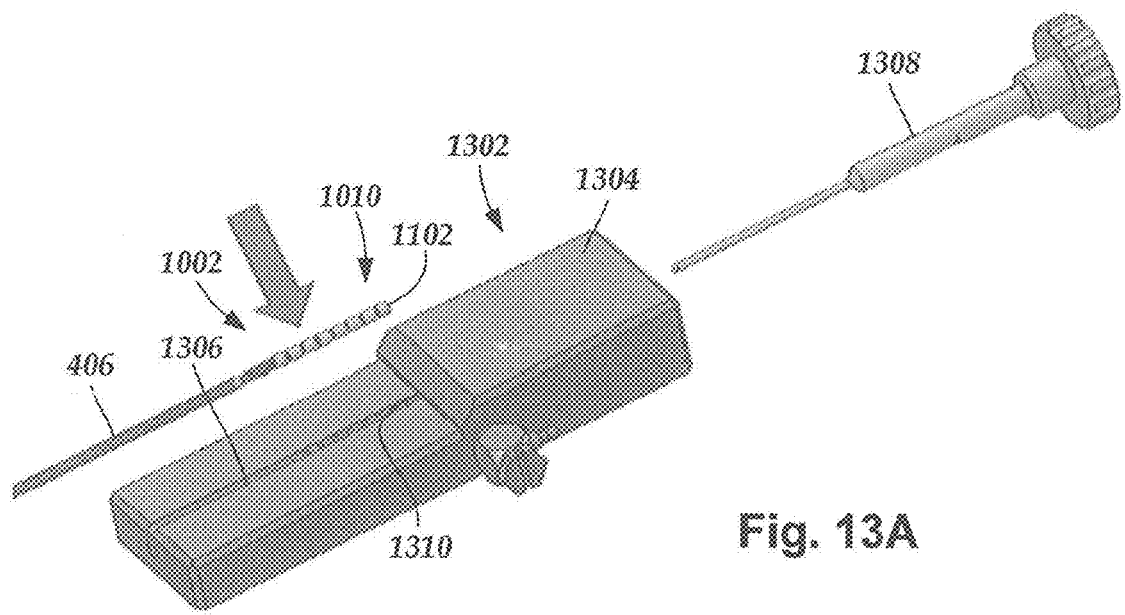
FIG. 13A is a schematic perspective view of one embodiment of a laser-welding fixture and the composite structure of FIG. 12A, where the lead-body conductors of FIG. 12B are inserted into the lead body of FIG. 9, where the electrodes of FIG. 12A are disposed over portions of the composite structure, and where the laser-welding fixture is configured and arranged to facilitate electrical coupling of the electrodes to the micro-circuits of the composite structure, according to the invention.
Figure 13B:
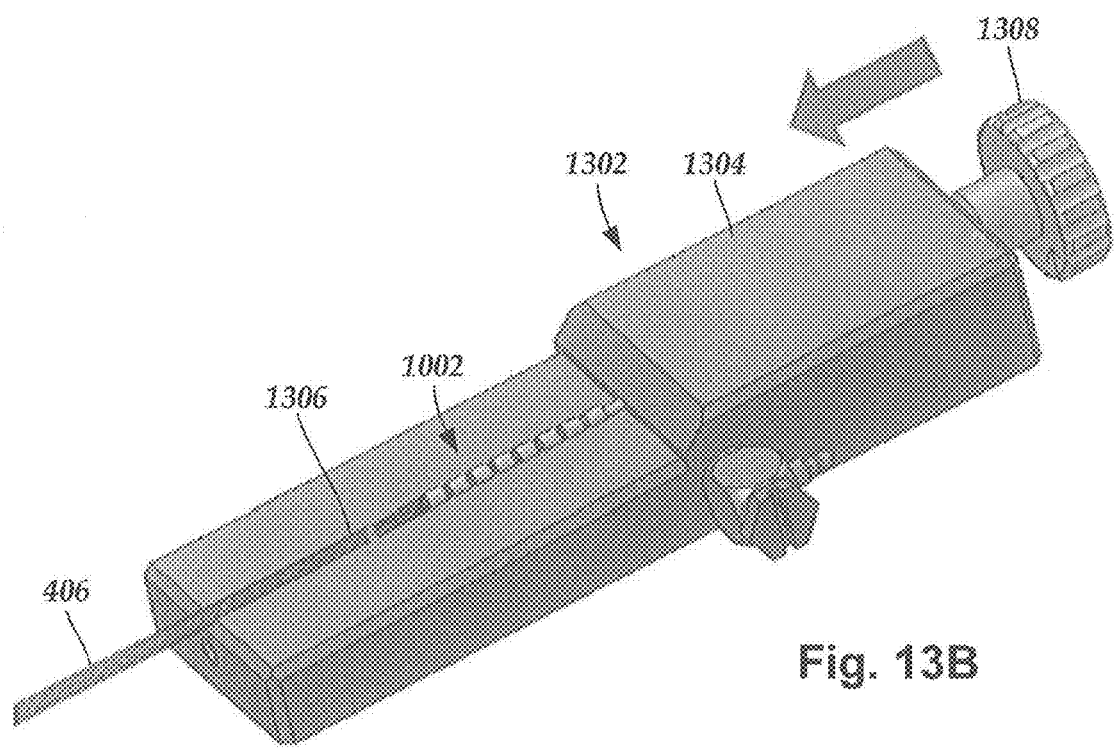
FIG. 13B is a schematic perspective view of one embodiment of the composite structure of FIG. 13A disposed in a channel of the laser-welding fixture of FIG. 13A to facilitate electrical coupling of the electrodes of FIG. 13A to the micro-circuits of the composite structure, according to the invention.

Turning to FIGS. 13A-13B, the aligned electrodes 434 can be electrically coupled to the composite structure 1002 to form a contact pre-assembly. Contacts, such as the electrodes 434, can be electrically coupled to the composite structure 1002 in any suitable manner including, for example, laser welding, crimping, or the like. FIGS. 13A-13B illustrate one embodiment of laser welding the electrodes 434 to the composite structure 1002 using a laser-welding fixture.

FIG. 13A is a schematic perspective view of one embodiment of the rolled-up composite structure 1002 and a laser-welding fixture 1302 configured to receive the composite structure 1002. The electrodes 434 are disposed over the rolled-up composite structure 1002 and aligned with the contact interfaces 544a and 544b of the composite structure 1002. In FIG. 13A, the lead-body conductors 408 are shown attached to the composite structure 1002 and are extended along the lead body 406.

The laser-welding fixture 1302 is configured and arranged to facilitate electrically coupling of the electrodes 434 to the contact interfaces 544 of the micro-circuits 544a and 544b of the composite structure 1002. In at least some embodiments, the laser-welding fixture 1302 includes a body 1304 that defines a channel 1306 configured to receive the rolled-up composite structure 1002. A mandrel 1308 is configured and arranged for insertion into an aperture 1310 defined through a portion of the base 1304 that extends along one end of the channel 1306. The aperture 1310 is positioned such that one end of the aperture 1310 is aligned with an end of the channel 1306. In at least some embodiments, the aperture 1310 is positioned such that when the mandrel 1308 is extended through the aperture 1310, the mandrel 1308 may be further extended through the bore 1102 along the first end portion 1010 of the rolled-up composite structure 1002.

FIG. 13B is a schematic perspective view of one embodiment of the composite structure 1002 and the laser-welding fixture 1302. In FIG. 13B, the composite structure 1002 is disposed in the channel 1306 and the mandrel 1308 is inserted into the aperture 1310 such that the mandrel 1308 extends completely through the aperture 1310 and into the bore 1102 of the rolled-up composite structure 1002 at the first end portion 101 of the composite structure 1002. In at least some embodiments, disposing the composite structure 1002 in the channel 1306 and inserting the mandrel 1308 into the bore 1102 of the composite structure 1002 provides physical support to the composite structure 1002 and the electrodes 434 for facilitating laser welding of the electrodes 434 to the contact interfaces 544 of the composite structure 1002.

In at least some embodiments, such as embodiments where the composite structure 1002 is disposed at a distal end of a percutaneous lead, a plug ball is inserted into the distal tip of the lead. The plug ball may be useful, for example, to prevent undesired coring of patient tissue during placement of the lead by functioning as an end stop for a stylet lumen defined along the lead body 406. The plug ball may also be useful to form a blunt distal tip of the lead during an over-molding process.

Figure 14A:
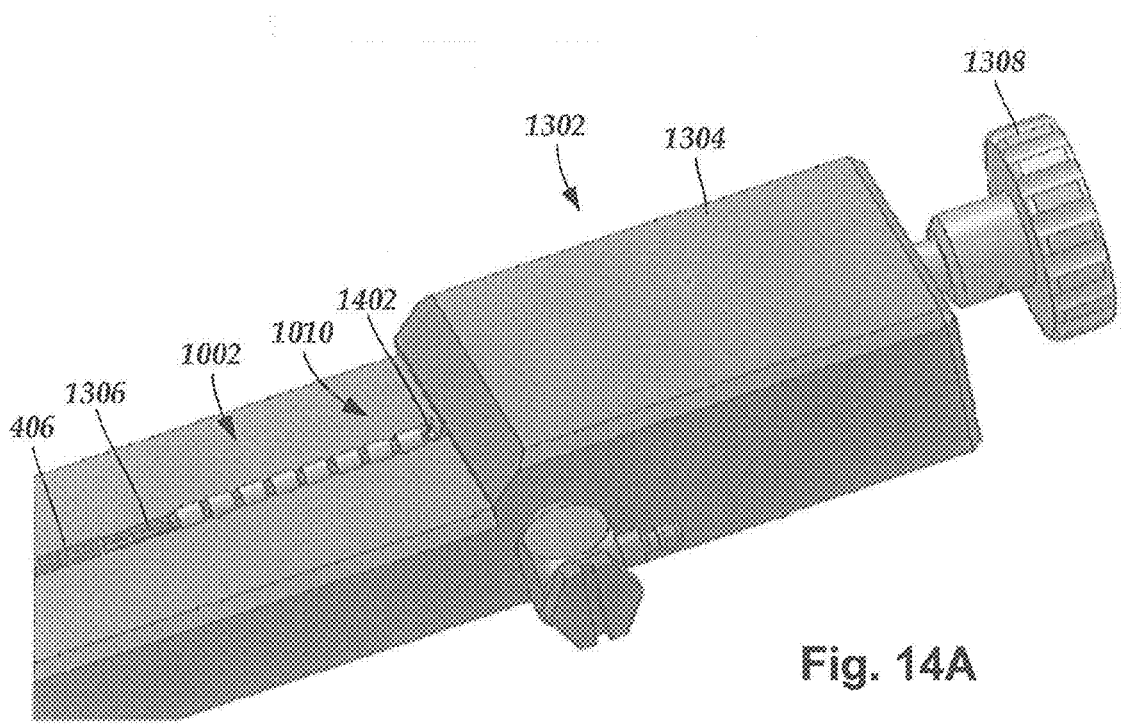
FIG. 14A is a schematic perspective view of one embodiment of the composite structure of FIG. 13B disposed in a channel of the laser-welding fixture of FIG. 13A to facilitate insertion of a plug ball into an end portion of the composite structure, according to the invention.

FIG. 14A is a schematic perspective view of one embodiment of the composite structure 1002 and the laser-welding fixture 1302. In FIG. 14A, the composite structure 1002 is disposed in the channel 1306. A plug ball 1402 is also positioned in the channel 1306. In FIG. 14A, the plug ball 1402 is shown positioned in the channel 1306 between the composite structure 1002 and the aperture 1310 (not shown in FIG. 14A) through which the mandrel 1308 extends.

Figure 14B:
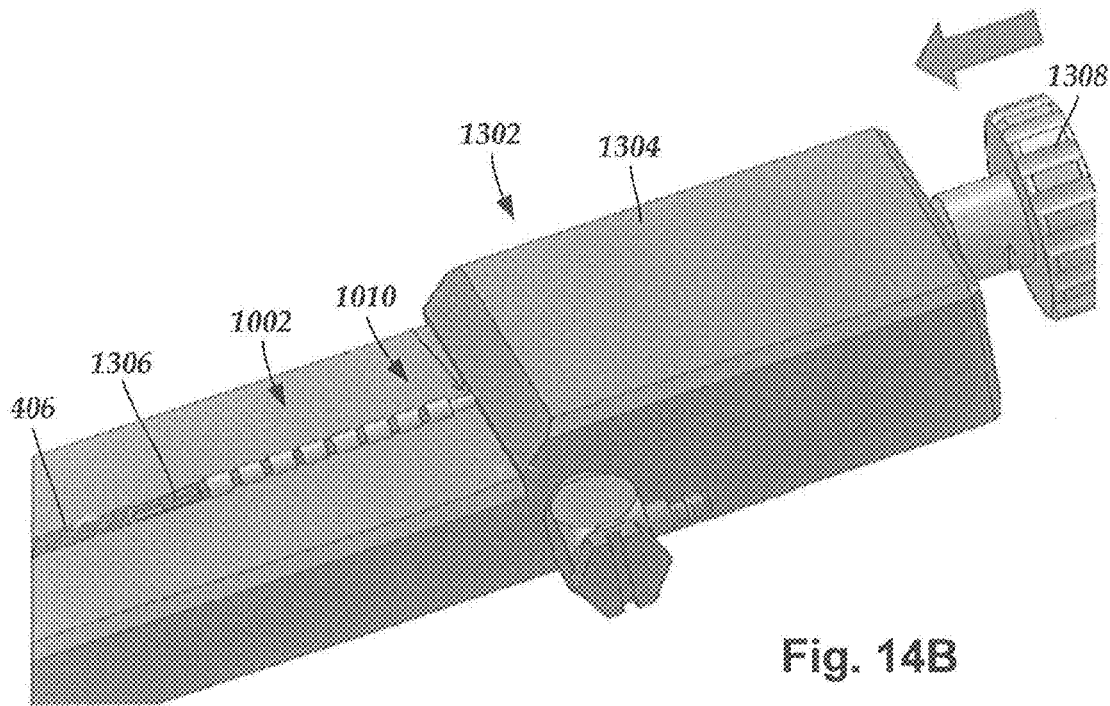
FIG. 14B is a schematic perspective view of one embodiment of the composite structure of FIG. 14A disposed in a channel of the laser-welding fixture of FIG. 13A, where a plug ball is being inserted into an end portion of the composite structure to form an end of a stylet lumen defined along the composite structure, according to the invention.

FIG. 14B is a schematic perspective view of one embodiment of the composite structure 1002 and the laser-welding fixture 1302. In FIG. 14B, the composite structure 1002 is disposed in the channel 1306. The mandrel 1308 is extended through the aperture 1310 and into the bore 1102 (not shown in FIG. 14B) at the first end portion 1010 of the composite structure 1002, thereby pressing the plug ball 1402 at least partially into the bore 1102 at the first end portion 1010 of the composite structure 1002.

Once contacts, such as the electrodes 434, are electrically coupled to the composite structure 1002, the contacts are mechanically coupled to the composite structure 1002. Additionally, the composite structure 1002 is mechanically coupled to the lead body. In at least some embodiments, the contacts are over-molded to the composite structure 1002. In at least some embodiments, the composite structure 1002 is over-molded to the lead body. Additionally, over-molding may be used to form electrically-nonconductive spacers between adjacent contacts.

Figure 15A:
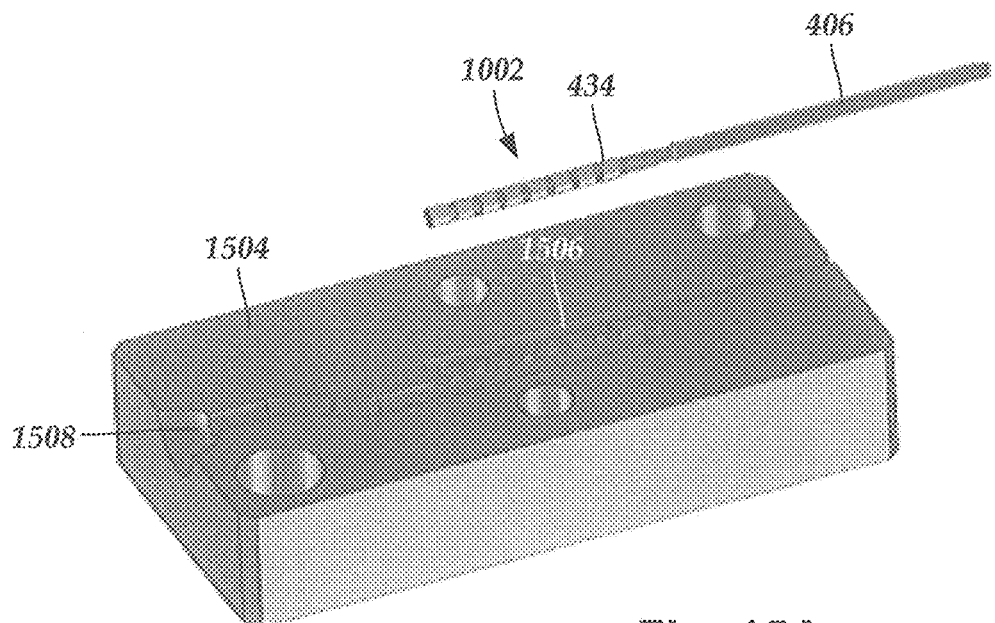
FIG. 15A is a schematic perspective view of one embodiment of a mold base, the composite structure of FIG. 14B, the electrodes of FIG. 14B electrically coupled to the composite structure, and the lead-body conductors of FIG. 13A attached to micro-circuits of the composite structure and inserted into the lead body of FIG. 13A, where the mold base is suitable for over-molding the composite structure for coupling the composite structure to the electrodes and to the lead body, according to the invention.
Figure 15B:
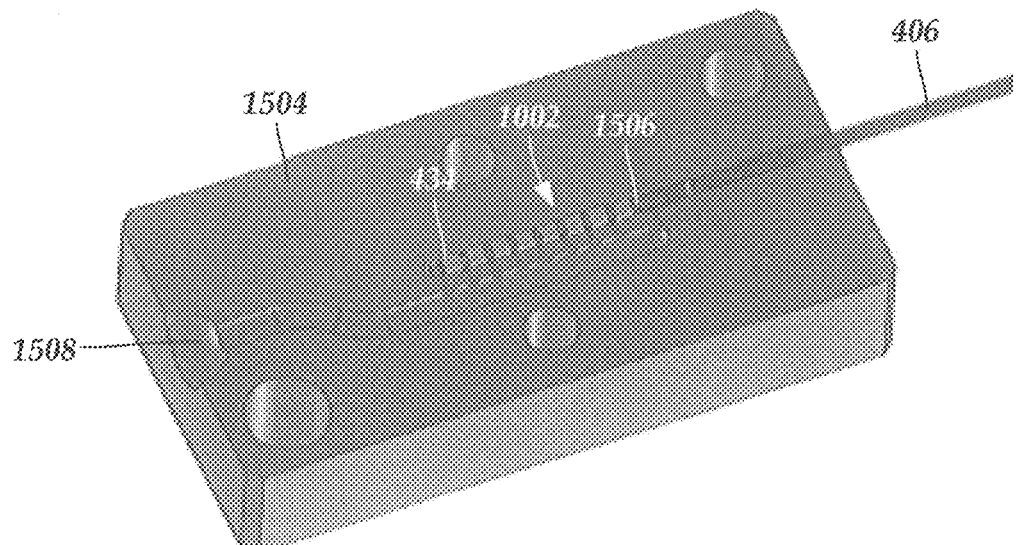
FIG. 15B is a schematic perspective view of one embodiment of the composite structure of FIG. 15A and the electrodes of FIG. 15A inserted into the mold base of FIG. 15A, according to the invention.

FIGS. 15A-15B illustrate one embodiment of an over-molding process suitable for one or more of: mechanically coupling the electrodes to the composite structure; mechanically coupling the composite structure to the lead body; and forming spacers between adjacent electrodes. FIG. 15A is a schematic perspective view of one embodiment of the composite structure 1002 with the electrodes 434 electrically coupled thereto, and a mold base 1504 suitable for injection molding. The mold base 1504 defines a pocket 1506 suitable for receiving the composite structure 1002, and an injection port 1508 for injecting a suitable material into the pocket 1506 for over-molding the composite structure 1002 when the composite structure 1002 is disposed in the pocket 1506.

FIG. 15B is a schematic perspective view of one embodiment of the composite structure 1002 disposed in the pocket 1506 of the mold base 1504. Any electrically-non-conductive, implantable material suitable for: mechanically coupling the electrodes to the composite structure; mechanically coupling the composite structure to the lead body; or forming spacers between adjacent electrodes may be used.

Figure 16:
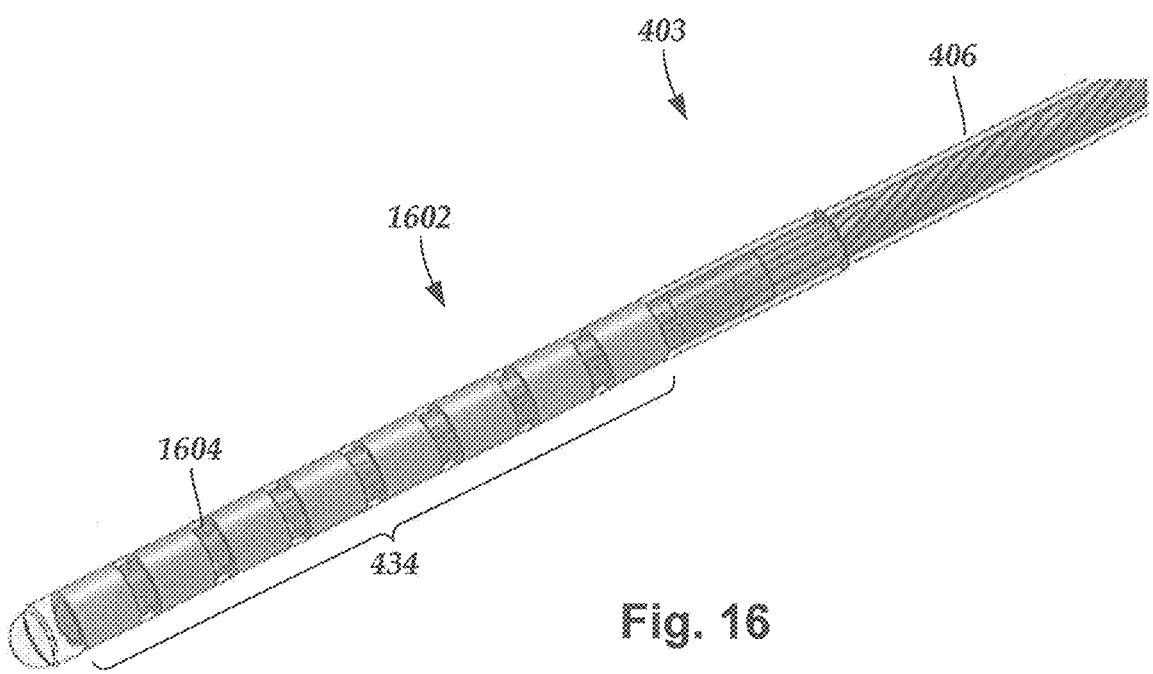
FIG. 16 is a schematic perspective view of one embodiment of a contact pre-assembly formed by over-molding the composite structure of FIG. 15B, the contact pre-assembly configured and arranged to form the contact assembly of FIG. 4 when ground down, according to the invention.

Once the composite structure 1002 is over-molded to form electrically-non-conductive spacers between adjacent contacts, the contacts and the layered element are collectively referred to herein as a contact pre-assembly. FIG. 16 is a schematic perspective view of one embodiment of the lead 403. The lead 403 includes one embodiment of a pre-contact assembly 1602 coupled along an end portion of the lead body 406. In at least some embodiments, the pre-contact assembly 1602 includes spacers, such as spacer 1604, disposed between adjacent electrodes 434 of the pre-contact assembly 1602. As shown in FIG. 16, in at least some embodiments, once the enhanced composite structure 1002 is over-molded to form the pre-contact assembly 1602, the pre-contact assembly 1602 may have a diameter that is larger than a diameter of the lead body 406. Additionally, the pre-contact assembly 1602 may have non-conductive material disposed over portions of outer surfaces of the electrodes 434. In which case, the pre-contact assembly 1602 may, optionally, be ground down to form the contact assembly 402 (see e.g., FIG. 4). In at least some embodiments, the pre-contact assembly 1602 is ground down such that the formed contact assembly 402 is isodiametric with the lead body 406.

As mentioned above, the above-described techniques for forming the contact assembly have been described in terms of forming the contact assembly at the distal end of a percutaneous lead. It will be understood that the above-described techniques are equally applicable for forming a contact assembly at the proximal end of a lead (e.g., a percutaneous lead or a paddle lead). In at least some embodiments, a lead may have multiple enhanced contact assemblies. The above-described techniques are also equally applicable for forming ends of other elongated medical devices including, for example, lead extensions, splitters, adaptors, or the like.

Figure 17:
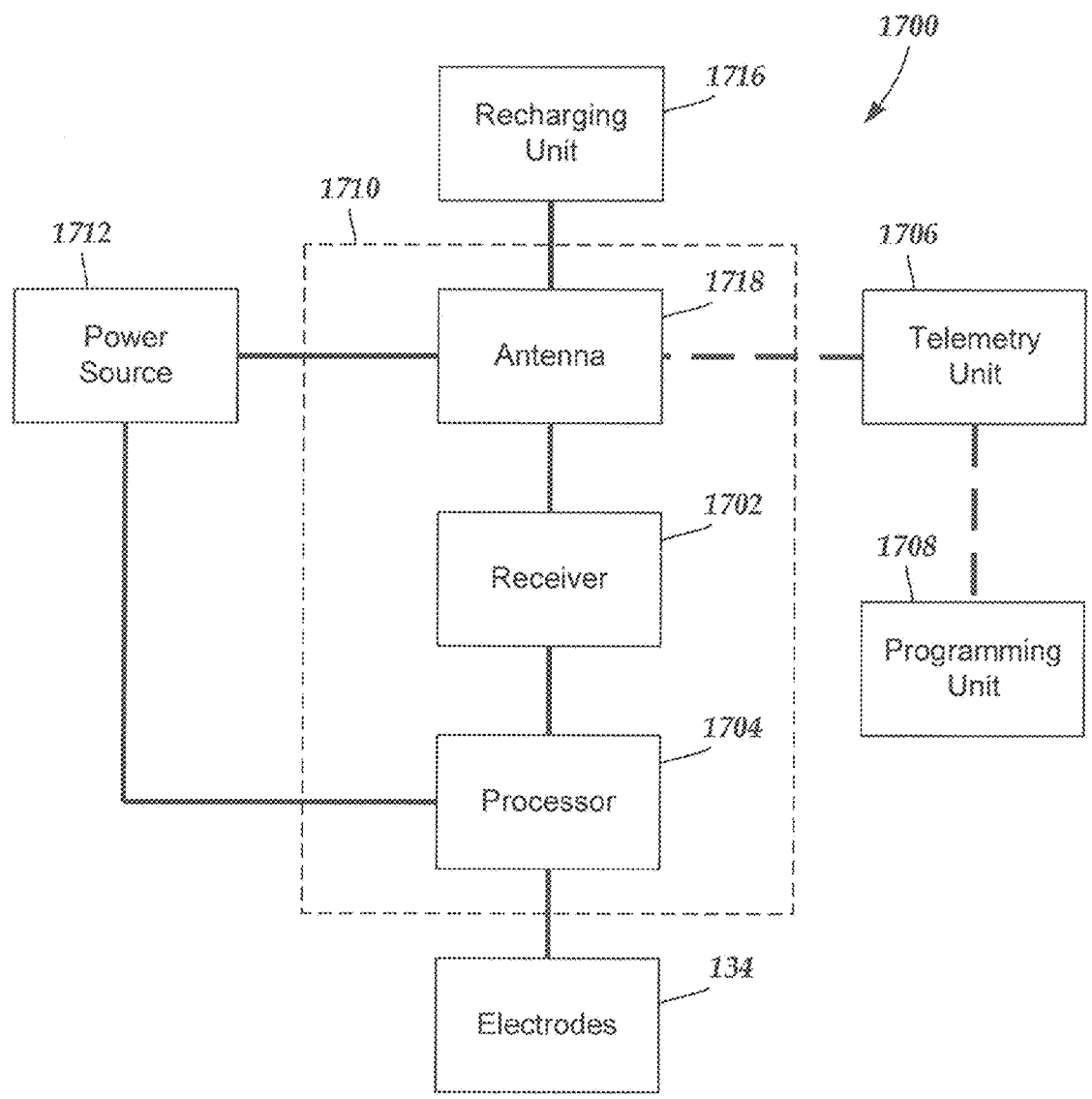
FIG. 17 is a schematic overview of one embodiment of components of a stimulation system, including an electronic subassembly disposed within a control module, according to the invention.

FIG. 17 is a schematic overview of one embodiment of components of an electrical stimulation system 1700 including an electronic subassembly 1710 disposed within a control module. It will be understood that the electrical stimulation system can include more, fewer, or different components and can have a variety of different configurations including those configurations disclosed in the stimulator references cited herein.

Some of the components (for example, power source 1712, antenna 1718, receiver 1702, and processor 1704) of the electrical stimulation system can be positioned on one or more circuit boards or similar carriers within a sealed housing of an implantable pulse generator, if desired. Any power source 1712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1718 or a secondary antenna. The external power source can be in a device that is mounted on the skin of the user or in a unit that is provided near the user on a permanent or periodic basis.

If the power source 1712 is a rechargeable battery, the battery may be recharged using the optional antenna 1718, if desired. Power can be provided to the battery for recharging by inductively coupling the battery through the antenna to a recharging unit 1716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1704 is generally included to control the timing and electrical characteristics of the electrical stimulation system. For example, the processor 1704 can, if desired, control one or more of the timing, frequency, strength, duration, and waveform of the pulses. In addition, the processor 1704 can select which electrodes can be used to provide stimulation, if desired. In some embodiments, the processor 1704 may select which electrode(s) are cathodes and which electrode(s) are anodes. In some embodiments, the processor 1704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1708 that, for example, allows modification of pulse characteristics. In the illustrated embodiment, the processor 1704 is coupled to a receiver 1702 which, in turn, is coupled to the optional antenna 1718. This allows the processor 1704 to receive instructions from an external source to, for example, direct the pulse characteristics and the selection of electrodes, if desired.

In one embodiment, the antenna 1718 is capable of receiving signals (e.g., RF signals) from an external telemetry unit 1706 which is programmed by a programming unit 1708. The programming unit 1708 can be external to, or part of, the telemetry unit 1706. The telemetry unit 1706 can be a device that is worn on the skin of the user or can be carried by the user and can have a form similar to a pager, cellular phone, or remote control, if desired. As another alternative, the telemetry unit 1706 may not be worn or carried by the user but may only be available at a home station or at a clinician's office. The programming unit 1708 can be any unit that can provide information to the telemetry unit 1706 for transmission to the electrical stimulation system 1700. The programming unit 1708 can be part of the telemetry unit 1706 or can provide signals or information to the telemetry unit 1706 via a wireless or wired connection. One example of a suitable programming unit is a computer operated by the user or clinician to send signals to the telemetry unit 1706.

The signals sent to the processor 1704 via the antenna 1718 and receiver 1702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1700 to cease operation, to start operation, to start charging the battery, or to stop charging the battery. In other embodiments, the stimulation system does not include an antenna 1718 or receiver 1702 and the processor 1704 operates as programmed.

Optionally, the electrical stimulation system 1700 may include a transmitter (not shown) coupled to the processor 1704 and the antenna 1718 for transmitting signals back to the telemetry unit 1706 or another unit capable of receiving the signals. For example, the electrical stimulation system 1700 may transmit signals indicating whether the electrical stimulation system 1700 is operating properly or not or indicating when the battery needs to be charged or the level of charge remaining in the battery. The processor 1704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
   a lead body having a distal end portion and a proximal end portion;
   a plurality of first contacts disposed along one of the distal end portion or the proximal end portion of the lead body;
   a contact assembly disposed along the other of the distal end portion or the proximal end portion of the lead body, the contact assembly comprising
      a plurality of micro-circuits laminated to a first electrically-nonconductive substrate and rolled into a tube, the micro-circuits each having a first end portion and an opposing second end portion, wherein a plurality of through-holes are defined through the first electrically-nonconductive substrate with at least one through-hole disposed between each adjacent pair of the micro-circuits, and
      a plurality of second contacts disposed over the tube formed by the plurality of micro-circuits and the first electrically-nonconductive substrate, wherein each of the second contacts is electrically coupled to the first end portion of at least one of the plurality of micro-circuits; and
      a plurality of lead-body conductors electrically coupling the plurality of first contacts to the plurality of second contacts, wherein each of the plurality of lead-body conductors is attached to the second end portion of at least one of the plurality of micro-circuits.

2. The electrical stimulation lead of claim 1, further comprising a second electrically-nonconductive substrate, wherein at least a portion of each of the micro-circuits is laminated between the first and second electrically-nonconductive substrates.

3. The electrical stimulation lead of claim 1, wherein the plurality of first contacts are terminals disposed along the proximal end portion of the lead body and the plurality of second contacts are electrodes disposed along the contact assembly.

4. The electrical stimulation lead of claim 1, wherein the plurality of first contacts are electrodes disposed along the distal end portion of the lead body and the plurality of second contacts are terminals disposed along the contact assembly.

5. The electrical stimulation lead of claim 1, wherein each of the first electrically-nonconductive substrates comprises a thermoplastic material.

6. The electrical stimulation lead of claim 1, wherein the contact assembly further comprises a severed end of a conductor tie bar attached to at least one of the plurality of micro-circuits, wherein the severed end terminates at a one of the through-holes.

7. The electrical stimulation lead of claim 1, wherein the plurality of micro-circuits comprise MP35N.

8. The electrical stimulation lead of claim 1, wherein the lead is a percutaneous lead.

9. The electrical stimulation lead of claim 1, wherein the lead is a paddle lead.

10. The electrical stimulation lead of claim 1, wherein the contact assembly is a first contact assembly, and further comprising a second contact assembly disposed along the opposing end portion of the lead body.

11. An electrical stimulating system comprising:
    the electrical stimulation lead of claim 1;
    a control module coupleable to the electrical stimulation lead, the control module comprising
       a housing, and
       an electronic subassembly disposed in the housing; and
    a connector for receiving the electrical stimulation lead, the connector having a proximal end, a distal end, and a longitudinal length, the connector comprising
       a connector housing defining a port at the distal end of the connector, the port configured and arranged for receiving the proximal end portion of the lead body, and
       a plurality of connector contacts disposed in the connector housing, the plurality of connector contacts configured and arranged to couple to at least one of the plurality of terminals disposed on the proximal end portion of the lead body of the electrical stimulation lead.

12. A method of forming an electrical stimulation lead, the method comprising:
    forming a contact assembly comprising a plurality of micro-circuits laminated to at least one electrically-nonconductive substrate, wherein each of the micro-circuits has a first end portion and an opposing second end portion and each of the micro-circuits is coupled to at least one adjacent micro-circuit by a conductor tie bar;
severing the conductor tie bars and forming a plurality of through-holes through the at least one electrically-nonconductive substrate;
exposing a contact interface along the first end portion of each of the plurality of micro-circuits;
mechanically coupling a plurality of contacts to the contact assembly; and
electrically coupling each of the contacts to the exposed contact interface of a one of the plurality of micro-circuits.

13. The method of claim 12, wherein mechanically coupling a plurality of contacts to the contact assembly comprises rolling the contact assembly into a tubular-shape and disposing the plurality of contacts over the tubular-shaped contact assembly.

14. The method of claim 12, wherein electrically coupling each of the contacts to the exposed contact interfaces of the plurality of micro-circuits comprises laser welding at least one of the contacts to at least one of the contact interfaces.

15. The method of claim 12, wherein mechanically coupling a plurality of contacts to the contact assembly comprises over-molding the contact assembly after the contacts are electrically coupled to the contact interfaces of the plurality of micro-circuits.

16. The method of claim 12, further comprising
exposing a conductor interface along the second end portion of each of the plurality of micro-circuits; and
attaching a plurality of lead-body conductors to the exposed conductor interfaces of the plurality of micro-circuits.

17. An electrical stimulation lead, comprising:
a lead body having a distal end portion and a proximal end portion;
a plurality of first contacts disposed along one of the distal end portion or the proximal end portion of the lead body;
a contact assembly disposed along the other of the distal end portion or the proximal end portion of the lead body, the contact assembly comprising
a tubular-shaped composite structure comprising a plurality of layered elements mechanically coupled together and rolled into a tube, each of the plurality of layered elements comprises a first electrically-nonconductive substrate, and a plurality of micro-circuits laminated to the first electrically-nonconductive substrate, the micro-circuits each having a first end portion and an opposing second end portion, wherein a plurality of through-holes are defined through the first electrically-nonconductive substrate with at least one through-hole disposed between each adjacent pair of the micro-circuits, and
a plurality of second contacts disposed over the composite structure, wherein each of the second contacts is electrically coupled to the first end portion of at least one of the plurality of micro-circuits; and
a plurality of lead-body conductors electrically coupling the plurality of first contacts to the plurality of second contacts, wherein each of each of the plurality of lead-body conductors is attached to the second end portion of at least one of the plurality of micro-circuits.

18. The electrical stimulation lead of claim 17, wherein each of the layered elements further comprises a second electrically-nonconductive substrate, wherein at least a portion of each of the microcircuits is laminated between the first and second electrically-nonconductive substrates.

19. The electrical stimulation lead of claim 17, wherein the contact assembly further comprises a severed end of a conductor tie bar attached to at least one of the plurality of micro-circuits, wherein the severed end terminates at a one of the through-holes.

20. The electrical stimulation lead of claim 17, wherein the plurality of layered elements are stacked into at least two layers.

* * * * *